(12) United States Patent
Kagami et al.

(10) Patent No.: US 8,587,162 B2
(45) Date of Patent: Nov. 19, 2013

(54) ACTUATOR AND ELECTRIC TOOTHBRUSH UTILIZING SAME

(75) Inventors: Masaharu Kagami, Tokyo (JP); Kazutaka Sakaguchi, Tokyo (JP); Yuki Takahashi, Tokyo (JP); Shigenori Inamoto, Tokyo (JP)

(73) Assignee: Mitsumi Electric Co., Ltd., Tokyo (JP)

( * ) Notice: Subject to any disclaimer, the term of this patent is extended or adjusted under 35 U.S.C. 154(b) by 115 days.

(21) Appl. No.: 13/129,041

(22) PCT Filed: Nov. 10, 2009

(86) PCT No.: PCT/JP2009/005991
§ 371 (c)(1),
(2), (4) Date: May 12, 2011

(87) PCT Pub. No.: WO2010/055641
PCT Pub. Date: May 20, 2010

(65) Prior Publication Data
US 2011/0214239 A1 Sep. 8, 2011

(30) Foreign Application Priority Data
Nov. 14, 2008 (JP) .................................. 2008-292631

(51) Int. Cl.
*H02K 33/00* (2006.01)
(52) U.S. Cl.
USPC .............. 310/12.14; 310/15; 310/17; 310/36; 310/38; 310/112; 15/21.1
(58) Field of Classification Search
USPC ............. 310/12.14, 14–37, 38; 15/22.1, 22.2, 15/22.4, 23, 28
IPC ................ H02K 41/02,7/06, 7/65, 33/00, 35/00
See application file for complete search history.

(56) References Cited

U.S. PATENT DOCUMENTS 5,189,751 A 3/1993 Giuliani et al.
6,921,999 B1 * 7/2005 Stridsberg ................ 310/156.01
(Continued)

FOREIGN PATENT DOCUMENTS

JP  63-029604 A  2/1988
JP  08-065990 A  3/1996
(Continued)

OTHER PUBLICATIONS

Notice of reasons for rejecion for JP2008-292631, dated May 22, 2012.
Notice of the reasons for rejection dated Dec. 6, 2011.

*Primary Examiner* — John K Kim
*Assistant Examiner* — Michael Baraniecki
(74) *Attorney, Agent, or Firm* — Kubotera & Associates, LLC

(57) ABSTRACT

Disclosed is an actuator that realizes reciprocal rotational motion of an electric toothbrush, for example, without utilizing a drive transmission mechanism that is separate from the drive source. In the actuator, a fixed body (120) has a coil (128) that is disposed around a magnet (160) and faces the magnetic planes with different polarities within the magnet (160) at individual prescribed distances, and an outer yoke (150) that covers the outer periphery of the coil (128). The fixed body (120) rotatably supports a movable body (110), which holds the magnet (160), via a coil spring that is an elastic member (130) made from a wire. An alternating current supplying part (140) supplies an alternating current having roughly the same resonance frequency as that of the fixed body (120) to the coil (128) to cause the movable body (110) to vibrate in a reciprocal rotational motion. The coil spring that is the elastic member (130) uniformly disperses stress generated by the vibration.

5 Claims, 22 Drawing Sheets

(56) References Cited

U.S. PATENT DOCUMENTS

| | | | |
|---|---|---|---|
| 7,218,018 B2* | 5/2007 | Hasegawa et al. | 310/12.33 |
| 7,315,098 B2* | 1/2008 | Kunita et al. | 15/22.1 |
| 7,495,358 B2* | 2/2009 | Kobayashi et al. | 310/36 |
| 8,327,488 B2* | 12/2012 | Takahashi et al. | 15/22.1 |
| 2002/0195884 A1* | 12/2002 | Ichii et al. | 310/15 |
| 2004/0128781 A1* | 7/2004 | Kunita et al. | 15/22.2 |
| 2005/0235438 A1 | 10/2005 | Motohashi et al. | |
| 2007/0040457 A1* | 2/2007 | Shimizu et al. | 310/15 |
| 2010/0115718 A1 | 5/2010 | Shimizu et al. | |
| 2011/0203061 A1* | 8/2011 | Takahashi et al. | 15/22.1 |

FOREIGN PATENT DOCUMENTS

| | | |
|---|---|---|
| JP | 3243529 B | 1/2002 |
| JP | 2002-078310 A | 3/2002 |
| JP | 2002-176758 A | 6/2002 |
| JP | 2007-020589 A | 2/2007 |
| JP | 2007-082272 A | 3/2007 |
| JP | 2007-240728 A | 9/2007 |
| JP | 2008-058660 A | 3/2008 |
| JP | 2008-111882 A | 5/2008 |
| JP | 2008-178678 A | 8/2008 |

* cited by examiner

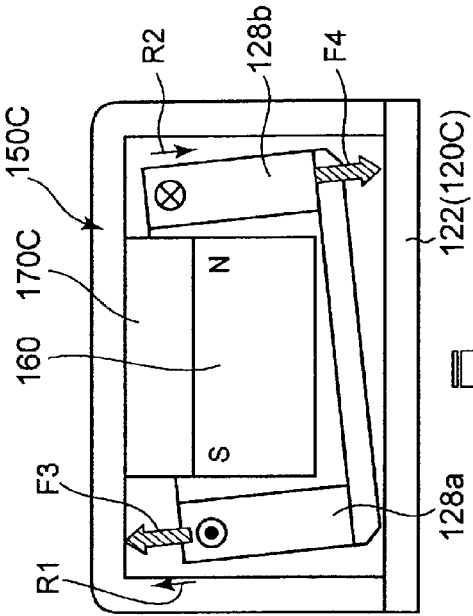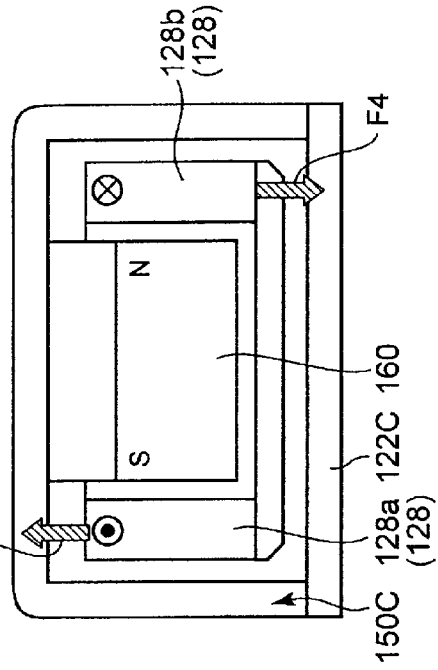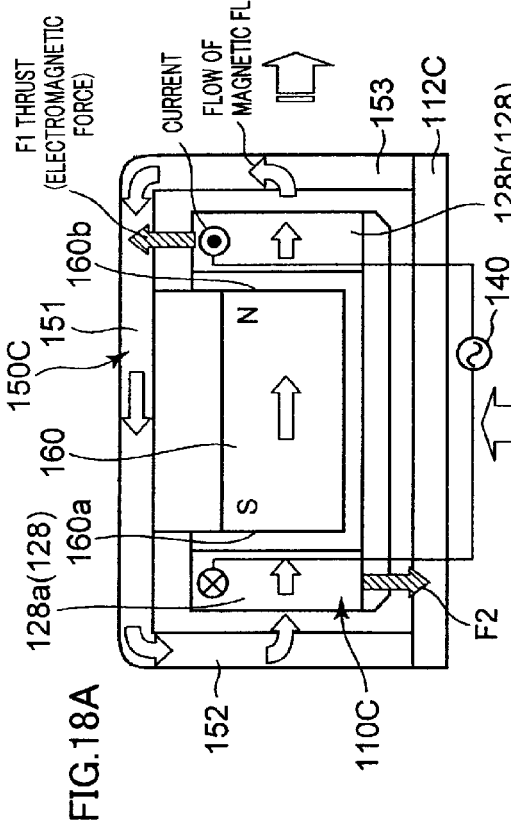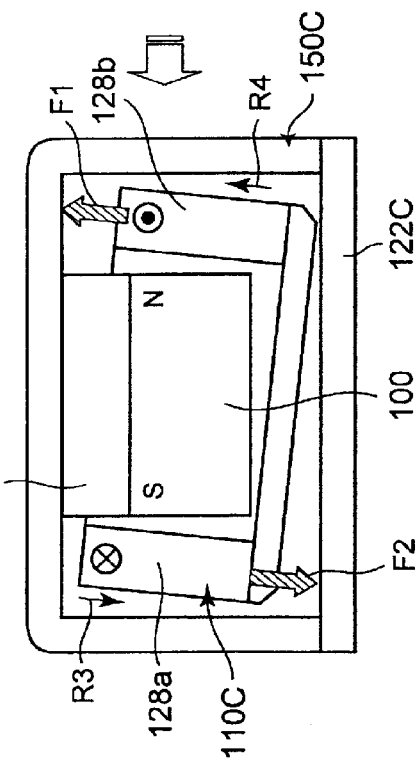

ACTUATOR AND ELECTRIC TOOTHBRUSH UTILIZING SAME

TECHNICAL FIELD

The present invention relates to an actuator used in, for example, an electric toothbrush or an electric sonic wave toothbrush.

BACKGROUND ART

Electric toothbrushes including electric sonic wave toothbrushes known heretofore include a bass brushing tooth brush places the brush in the part between the tooth and the gum at an angle (at an angle of approximately 45 degrees) and vibrates the brush to the right and left in back-and-forth linear motion, a rolling brushing toothbrush that rotates back and forth (forward and backward) over a predetermined angle range around a shaft and moves from the gum to the tooth rotating, and so on.

The drive of toothbrushes like these involves many structures for converting the rotation of a rotating DC motor that rotates regularly around a shaft into back-and-forth linear motion or back-and-forth rotating motion, via a motion direction converting mechanism. Furthermore, besides these structures, a structure to move a toothbrush in back-and-forth linear motion by means of a linear drive actuator, and a structure to move a toothbrush in back-and-forth rotating motion by making a resonance vibrating mechanism apart from the drive source resonate by the vibration of an actuator, are known.

With an electric toothbrush structured to move the brush part in back-and-forth linear motion by means of a linear drive actuator, as shown in patent literature 1, the linear actuator directly produces back-and-forth vibration in the axial direction of an output shaft that is directly connected with the brush part, and makes possible bass brushing. With this structure, there is little power loss due to a motion converting mechanism, and makes possible fast vibration.

Furthermore, with an electric toothbrush of a structure having an actuator and resonance vibrating mechanism apart from the drive source, as shown in patent literature 2, a drive means with an electro magnet and permanent magnet vibrates the resonance vibrating mechanism having a lever arm. By this means, the lever arm that is coaxially connected with the brush part moves in swinging motion, making possible rolling brushing.

CITATION LIST

Patent Literature

PTL 1
Japanese Patent Application Laid-Open No. 2002-078310
PTL 2
Japanese Patent Publication No. 3243529

SUMMARY OF INVENTION

Technical Problem

Now, to make possible rolling brushing with an electric toothbrush and to make the handle part in which the drive part to drive a rolling brushing toothbrush is accommodated as thin as possible, there is a demand to miniaturize the toothbrush drive part.

However, to realize rolling brushing using a regular motor that rotates around a shaft, apart from this motor, a motion direction converting mechanism to covert the rotation of this motor into back-and-forth rotating motion is necessary. Also, to realize rolling brushing using a linear drive actuator as shown in patent literature 1, apart from this linear drive actuator, a torque generating mechanism (drive source) is necessary.

Also, the structure shown in patent literature 2 requires a drive source as well as a resonance vibrating mechanism apart from the drive source.

Consequently, with conventional structures, if a motor or a linear drive actuator is used as a drive source of an electric toothbrush, it is necessary to secure a space for placing a drive source, and, in addition, a motion direction converting mechanism, a torque generating mechanism, or a resonance vibrating mechanism, apart from the drive source, and there is therefore problem that it is difficult to miniaturize the toothbrush.

In addition, in the event a drive transmitting mechanism (e.g. motion direction converting mechanism) is provided apart from an actuator (e.g. motor) as a toothbrush drive part, there is a threat of producing noise in the drive transmitting mechanism and there is furthermore a threat that the drive transmitting mechanism suffers poor efficiency due to power loss, and it is necessary to take measures against these.

It is an object of the present invention to provide a small actuator and electric toothbrush that can realize back-and-forth rotating motion of an electric toothbrush or the like without using a drive transmitting mechanism apart from a drive source.

Solution to Problem

An actuator according to the present invention adopts a configuration having: an outer yoke having inner wall planes that are placed a predetermined interval apart opposing each other; a permanent magnet that is placed to oppose the opposing inner wall planes over an air gap and that has different magnetic pole planes that oppose the inner wall planes respectively; and a coil that is placed in the air gap and surrounds the permanent magnet, and this actuator further has: a fixed body that has one of the permanent magnet and the coil; a movable body that has the other one of the permanent magnet and the coil and that has an output shaft that is perpendicular to both a direction in which the magnetic pole planes and the inner wall planes oppose each other and an axial direction of winding of the coil; an alternating current supplying section that supplies an alternating current of approximately a same frequency as a resonance frequency of the movable body to the coil; and a linear elastic member that has its one end fixed to the fixed body and the other end fixed to the movable body, and that supports the movable body on the fixed body to be able to rotate about an axis along the output shaft.

An electric toothbrush according to the present invention adopts a configuration having: an actuator of the above configuration; and a toothbrush part that is coaxially coupled with the output shaft of the actuator, at a head of the toothbrush part a hair bundle part being provided to be perpendicular to an axial direction.

Advantageous Effects of Invention

According to the present invention, it is possible to achieve back-and-forth rotating motion of an electric toothbrush or the like without using a drive transmitting mechanism apart from a drive source.

BRIEF DESCRIPTION OF DRAWINGS

FIG. 18 is a schematic view for explaining operation of an actuator according to the fourth embodiment of the present invention;

DESCRIPTION OF EMBODIMENTS

Now, embodiments of the present invention will be described below in detail with reference to the accompanying drawings.

First Embodiment

Figure 1:
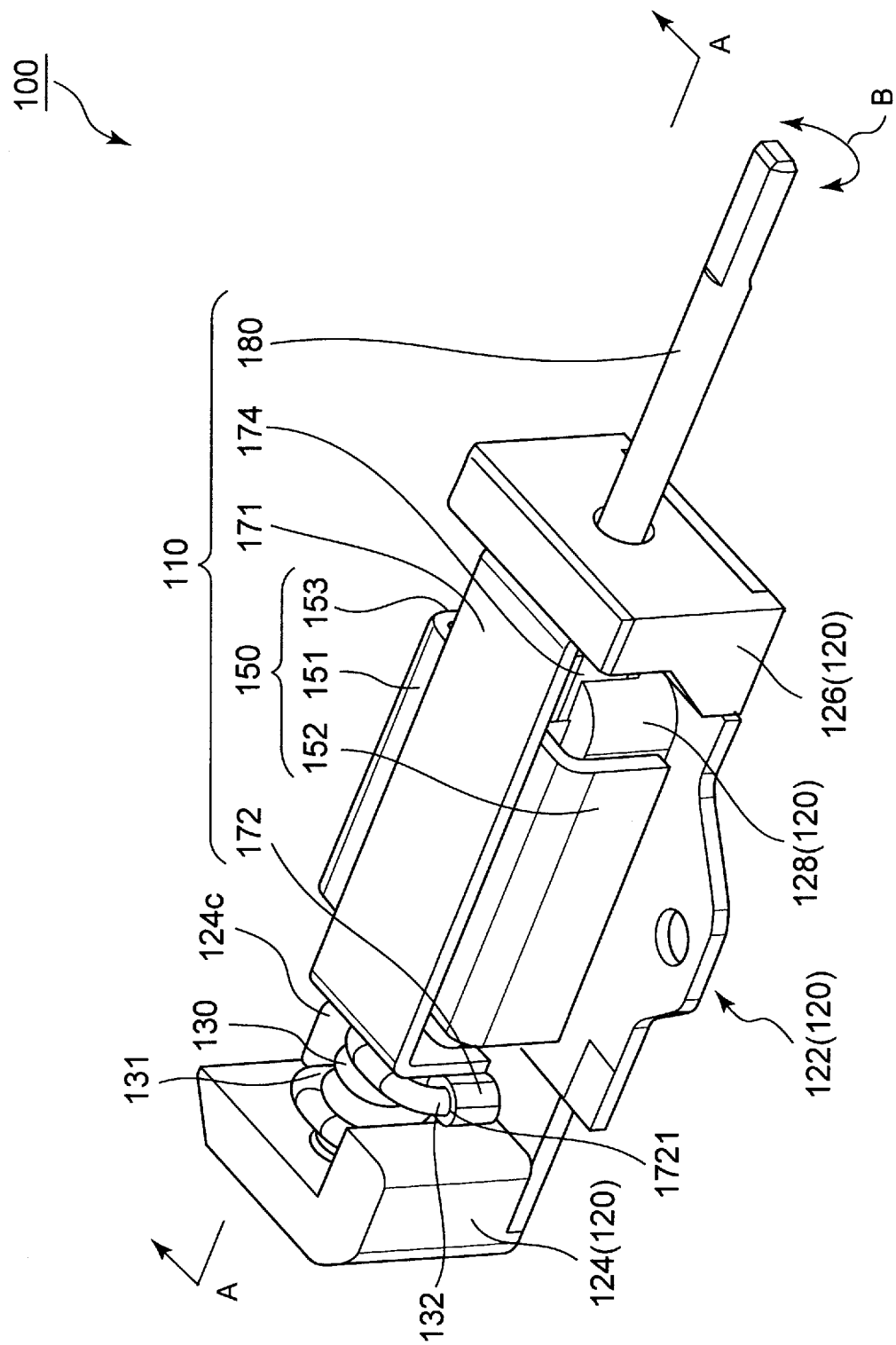
FIG. 1 is a perspective view showing an actuator according to the first embodiment of the present invention.
Figure 2:
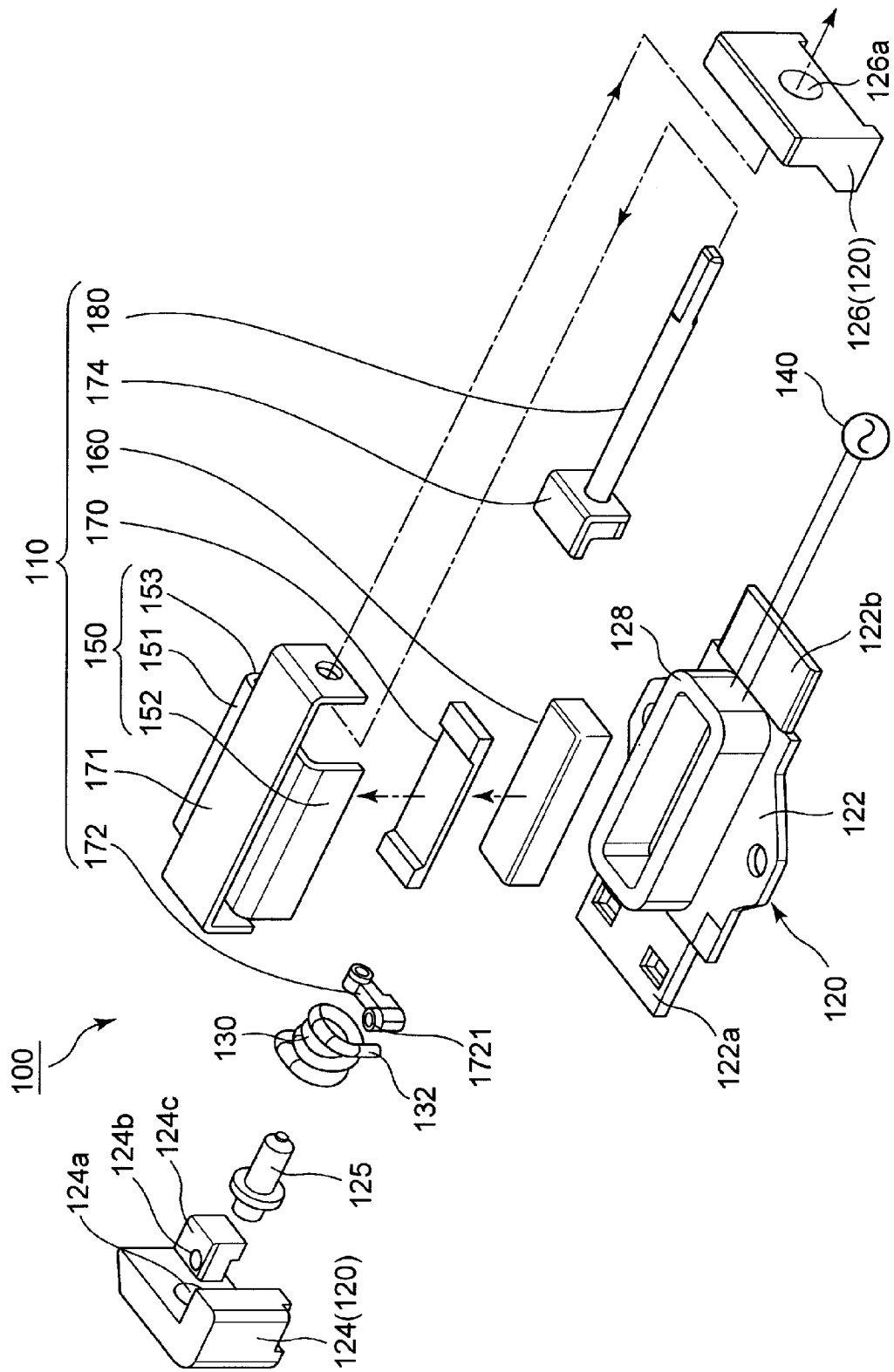
FIG. 2 is a perspective view showing a state an outer yoke is removed from this actuator.

FIG. 1 is a perspective view showing actuator 100 according to the first embodiment of the present invention, and FIG. 2 is a principal-part perspective view of this actuator 100.

Actuator 100 shown in FIG. 1 and FIG. 2 has movable body 110, fixed body 120, elastic member 130 that supports movable body 110 on fixed body 120 in a movable fashion, and alternating current supplying part 180 (see FIG. 2). Movable body 110 has outer yoke 150, magnet 160, yoke holder 171, and output shaft 180, which is a back-and-forth rotating vibration transmission shaft, and fixed body 120 has base plate 122, support wall parts 124 and 126 and coil 128 (see FIG. 2).

With actuator 100 shown in FIG. 1, in fixed body 120, an alternating current is supplied from alternating current supplying part 140 to coil 128 that is provided in a center part on the surface of base plate 122. By this means, movable body 110, which has magnet 160 that is placed on the inner side of coil 128 and which is supported by fixed body 120 via linear elastic member 130, is driven (moves) in a resonant state. When this movable body 110 moves, output shaft 180 of movable body 110 rotates in forward and backward directions (the directions of arrow B in FIG. 1) in a predetermined angle range, and outputs back-and-forth rotating vibration outside.

Figure 3:
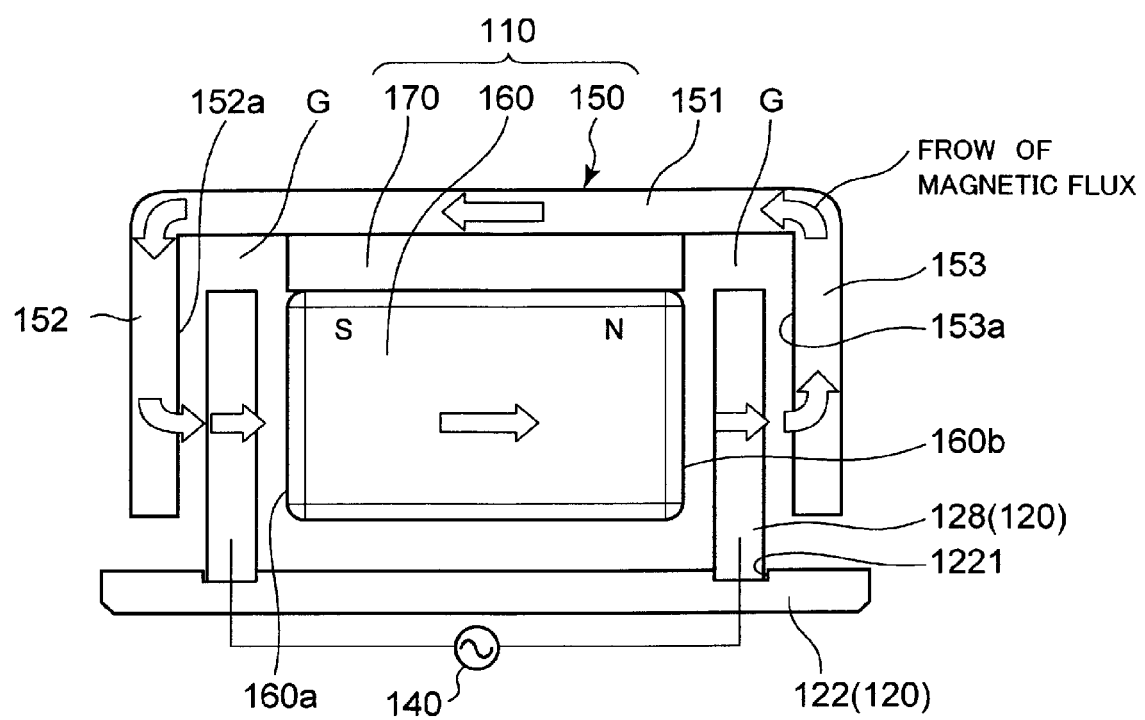
FIG. 3 is a schematic cross-sectional view showing configurations of a movable body and fixed body of this actuator.

FIG. 3 is a schematic cross-sectional view showing configurations of movable body 110 and fixed body 120 of actuator 100.

As shown in FIG. 1 to FIG. 3, outer yoke 150 has a cross section that is virtually U-shaped and is open downward, and is formed by bending a flat magnetifc body. Outer yoke 150 has yoke center part 151 of a flat rectangular shape, and mutually opposing sidewall parts 152 and 153 that hang from the side parts of yoke center part 151.

In the center area on the back of yoke center part 151 of outer yoke 150, magnet 160 is placed via non-magnetic body 170, such that air gaps are formed between magnet 160 and opposing sidewall parts 152 and 153 of outer yoke 150.

Magnet 160 is provided to hang from yoke center part 151, via non-magnetic body 170, and different magnetic poles face inner wall planes 152a and 153a of sidewall parts 152 and 153.

That is to say, here, the S-pole end of magnet 160 faces inner wall plane 152a of sidewall part 152 of outer yoke 150, and the N-pole side faces inner wall plane 153a of sidewall part 153 of outer yoke 150.

Furthermore, magnet 160 is a cuboid having a length to match the length of the extension direction of outer yoke 150, and is attached to the back of yoke center part 151, via non-magnetic body 170 having the same bottom surface shape, along the extension direction of yoke center part 151.

Magnet 160 thus turns planes of different magnetic poles to all of inner wall planes 152a and 153a of side wall parts 152 and 153 that extend in the long direction of outer yoke 150. Magnet 160 may also be placed in outer yoke 150, without involving non-magnetic body 170, such that air gaps are formed between magnet 160 and opposing sidewall parts 152 and 153 of outer yoke 150.

In air gaps between magnet 160 and sidewall parts 152 and 153 of outer yoke 150, coil 128 that surrounds magnet 160 is placed spaced apart from all of side wall planes (magnetic pole planes) 160a and 160b of magnet 160, inner wall planes 152a and 153a of sidewall parts 152 and 153, and the back of yoke center part 151. That is to say, coil 128 of fixed body 120 is placed, in a non-contact fashion, in air gaps G between sidewall parts 152 and 153 and magnet 160.

Furthermore, as shown in FIG. 1 and FIG. 2, outer yoke 150, to which magnet 160 is attached, is fixed on yoke holder 171 on the surface of yoke center part 151.

Figure 4:
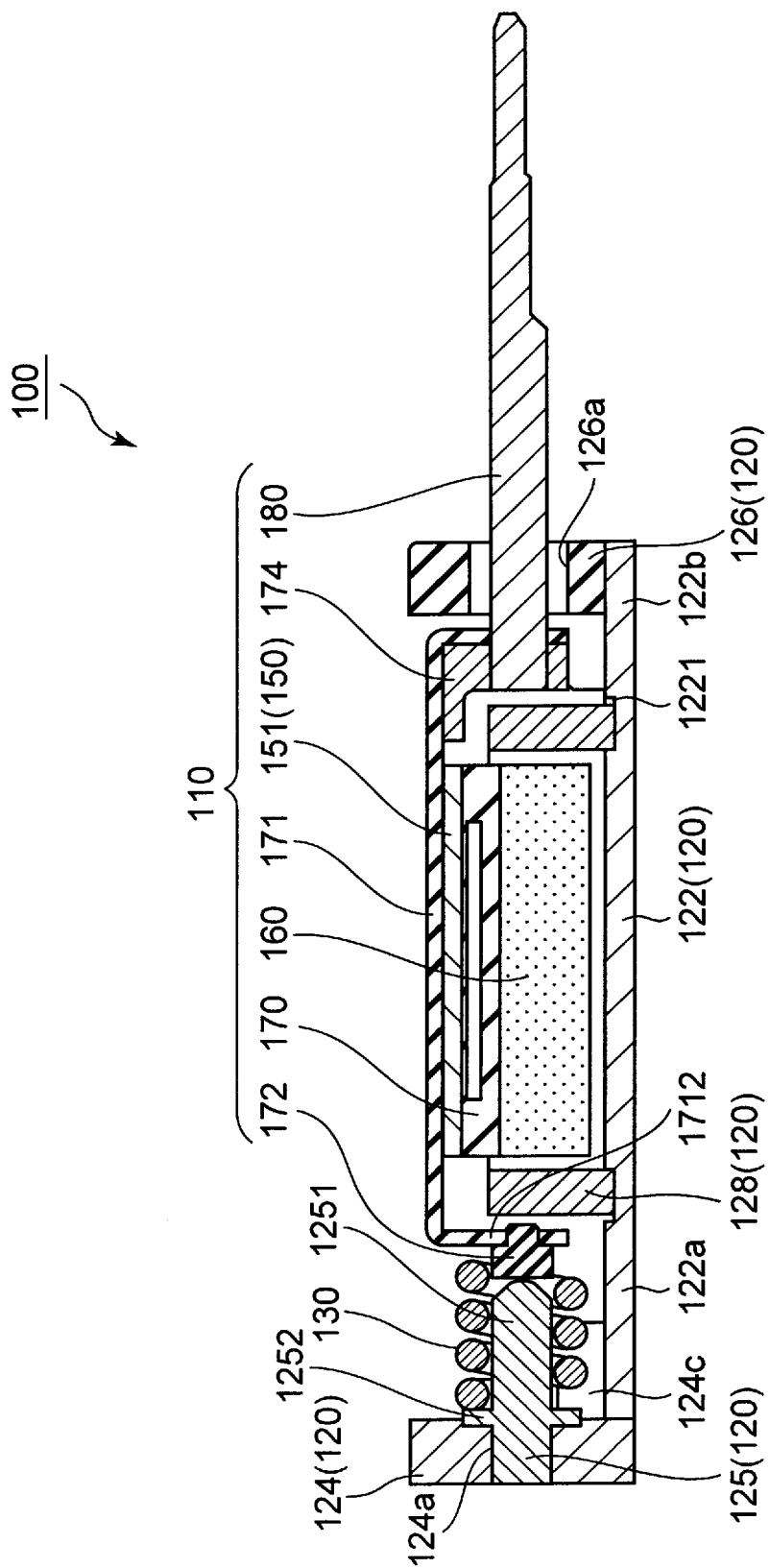
FIG. 4 is an arrow cross sectional view along line A-A in FIG. 1.

FIG. 4 is an arrow cross sectional view along line A-A in FIG. 1.

As shown in FIG. 2 and FIG. 4, in a long flat member that extends in the long direction of outer yoke 150 (corresponding the direction of the extension of output shaft 180), edge parts that are spaced part in the long direction are bent downward and form the shape of a letter U that is placed sideways on a side view. Output shaft attaching part 174, to which output shaft 180 is attached, is connected to the front end part of yoke holder 171. By this means, output shaft 180 is provided to project from the front end part of yoke holder 171, in the same direction as the direction of extension of outer yoke 150, that is, in a direction that is virtually perpendicular to the direction magnet 160 and sidewall parts 152 and 153 oppose each other.

Furthermore, joint part 172, which connects linear elastic member 130 that is connected to support wall part 124, is attached to the rear end part of yoke holder 171. Fitting hole 1721 is formed in joint part 172, and, in this fitting hole 1721, opposite end part 132 of a twisted coil spring, which is elastic member 130, is inserted. By this means, joint part 172 connects opposite end part 132 of elastic member 130 and yoke holder 171. Joint part 172 and output shaft attaching part 174 are preferably non-magnetic bodies.

Output shaft 180 is fixed to outer yoke 150 via output shaft attaching part 174 and yoke holder 171, and, by this means, is attached to movable body 110 to be located on an axis to pass the center of gravity of movable body 110. By this means, when movable body 110 moves in back-and-forth rotating vibration, output shaft 180 is able to transmit the vibration to the outside.

When actuator 100 is used for an electric toothbrush, a toothbrush part is coaxially coupled with output shaft 180, and, at the head of this toothbrush part, a hair bundle part is provided to be perpendicular to the axial direction. By this means the toothbrush part moves in the same motion as shaft 125, that is, moves in rolling motion, which is back-and-forth rotating vibration.

Coil 128 of fixed body 120 is a voice coil here, and is wound to surround magnet 160. To be more specific, in each air gap, coil 128 is wound in a direction perpendicular to the direction in which magnet 160 and sidewall parts 152 and 153 oppose each other.

Coil 128 is provided in fitting channel part 1221 (see FIG. 4) formed in the surface of base plate 122. Base plate 122 is a flat rectangular shape that is long in the direction in which output shaft 180 of movable body 110 extends, and, from the end parts (rear end part 122a and front end part 122b) of this base plate 122 spaced apart along the long direction, support wall parts 124 and 126 are erected.

As shown in FIG. 1, FIG. 2 and FIG. 4, support wall parts 124 and 126 are spaced apart in the long direction of base plate 122, and are provided in front and rear end parts 122a and 122b that project upward beyond the center part of base plate 122 where coil 128 is erected.

Support wall part 126 has opening part 126a in which output shaft 180 of movable body 110 is inserted, and, by inserting output shaft 180 in this opening part 126a, movable body 110 is supported to be able to rotate about output shaft 180.

Support wall part 124 supports elastic member 130 that is provided between support wall part 124 and joint part 172 of movable body 110. Via this elastic member 130, in a normal state, movable body 110 is supported virtually horizontally (that is, virtually parallel to base plate 122) by means of support wall parts 124 to be capable of back-and-forth rotating vibration.

In the area between opposing support wall parts 124 and 126, elastic member 130 supports movable body 110 in the twisting directions of magnet 160 and output shaft 180, such that movable body 110 is able to move in the front, back, left and right directions.

Figure 5:
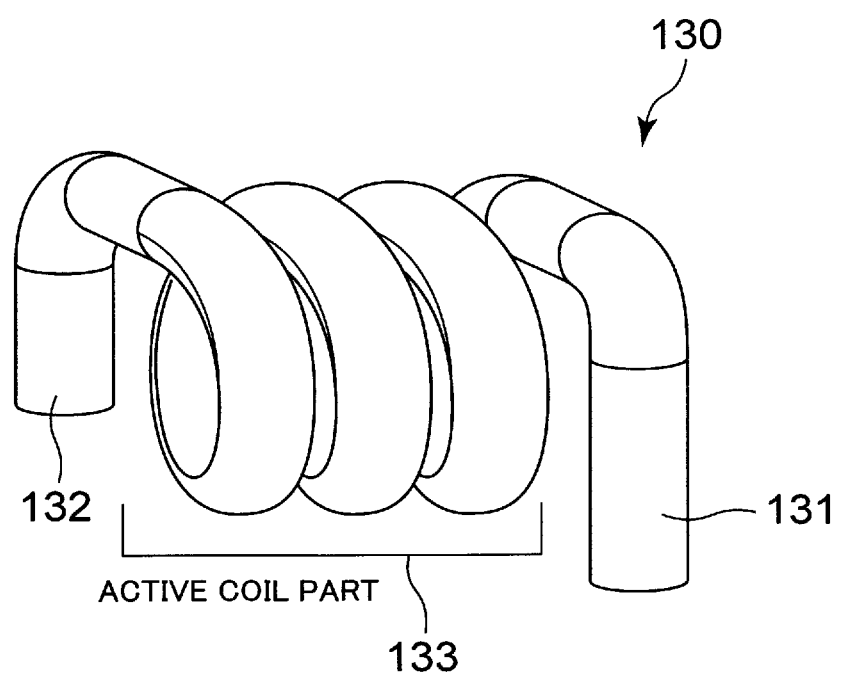
FIG. 5 is a perspective view of an elastic member.

FIG. 5 is a perspective view showing elastic member 130. As shown in FIG. 5, elastic member 130 is a coil spring that is formed with a linear wire element (linear member) that can be deformed elastically, has its end parts 131 and 132 bent in parallel and has active coil part 133 placed in the center part.

One end part 131 is inserted in insertion hole 124b formed in fixed block 124c of support wall part 124 shown in FIG. 2, and opposite end part 132 is inserted in fitting hole 1721 formed in joint part 172. By this means, in a state in which parts other than active coil part 133 are prevented from moving in peripheral directions and axial direction, elastic member 130 supports movable body 110 in fixed body 120 so as to be able to rotate about an axis along output shaft 180.

Also, as shown in FIG. 4, opening part 124a that is open toward movable body 110 is formed in support wall part 124, and, in this opening part 124a, guide shaft 125 that projects from support wall part 124 toward support wall part 126 is attached. In this guide shaft 125, projection part 1251 that projects from support wall part 124 forms a bar shape, and is inserted in a coil spring (i.e. elastic member 130) from one end. One end of the coil spring projects from the outer periphery on the base end side of projection part 1251, and contacts flanges 1252 which contact the inner wall plane of support wall part 124. By this means, support wall part 124, with guide shaft 125, receives one end part 131 of the coil spring, which is elastic member 130, and limits the movement of the coil spring (elastic member 130) in the radial direction.

By this means, the coil spring, which is elastic member 130, has its one end part 131 and opposite end part 132 fixed to support wall part 124 and joint part 172 attached to rear wall part 1712 of yoke holder 171. By this means, the coil spring, which is elastic member 130, is placed such that it can be compressed in the winding direction of the coil—that is, in the twisting directions—between support wall part 124 and joint part 172.

Via elastic member 130 configured in this way, movable body 110 is supported to be able to rotate in twisting directions.

Assuming that the inertia of movable body 110 is J and the spring constant in a twisting direction is $k_{sp}$, as compared with fixed body 120, movable body 110 vibrates in a resonance frequency calculated based on equation 1 below:

[1]

$$f_0 = \frac{1}{2\pi} \sqrt{\frac{K_{sp}}{J}} \quad (1)$$

In actuator 100 of the present embodiment, an alternating current of substantially the same frequency as resonance frequency $f_0$ of movable body 110 is supplied from alternating current supplying part 140 to coil 128. By this means, it is possible to drive movable body 110 efficiently.

In fixed body 120 and movable body 110, outer yoke 150, magnet 160 and coil 128 form a magnetic circuit.

As shown in FIG. 3, actuator 100 has a magnetic circuit where magnetic fluxes produced from magnet 160 (designated by outline arrows) pass an air gap where coil 170 is placed, sidewall part 153 of outer yoke 150, yoke center part 151, sidewall part 152 and the opposite air gap, in order.

Movable body 120 of this actuator 100 is a spring mass system structure that is supported by fixed body 120 via elastic member 130, and, when an alternating current of the same frequency as resonance frequency $f_o$ of movable body 110 is supplied to coil 128, movable body 110 is driven in a resonant state. The back-and-forth rotating vibration that is produced then is transmitted to output shaft 180 of movable body 110.

Actuator 100 is driven based on the equation of motion represented by equation 2 below and based on the circuit equation represented by equation 3 below.

[2]

$$J\frac{d^2\theta(t)}{dt^2} = K_t i(t) - K_{sp}\theta(t) - D\frac{d\theta(t)}{dt} - T_{Load} \qquad (2)$$

J: Inertia moment [Kgm2]
Θ(t): Angle [rad]
$K_t$: Torque constant [Nm/A]
i(t): Current [A]
$K_{sp}$: Spring constant [Nm/rad]
D: Attenuation coefficient [Nm/(rad/s)]
$T_{LOAD}$: Load torque [Nm]

[3]

$$e(t) = Ri(t) + L\frac{di(t)}{dt} + K_e\frac{d\theta(t)}{dt} \qquad (3)$$

e(t): Voltage [V]
R: Resistance [Ω]
L: Inductance [H]
$K_e$: Counter electromotive force multiplier [V/(rad/s)]

That is to say, the inertia moment, rotation angle, torque constant, current, spring constant, attenuation coefficient, and load torque in actuator 100 can be changed as adequate in a range to satisfy equation 2, and the voltage, resistance, inductance, and counter electromotive force multiplier can be changed as adequate in a range to satisfy equation 3.

Actuator 100 of this embodiment uses a coil spring as elastic member 130 to support movable body 110 in a movable fashion.

For example, when an elastic member such as flat spring is used as a member to support movable body 110 on fixed body 120 in a movable fashion, the distortion of the elastic member, (ε), increases as the rotation angle of the movable body increases. Also, the stress to apply to the elastic member increases following equation σ=Eε (E: the modulus of longitudinal elasticity of material) representing the relationship between stress (σ) and distortion (ε). When stress increases thus and the maximum stress value of the elastic material such as a flat spring becomes large, the elastic member is more likely to be fatigued. Consequently, it is possible to take measures by, for example, replacing the flat spring itself at an early time, applying processing such as drilling and bending to the flat spring to spread the stress and lower the maximum stress value, and so on. However, in the event the flat spring itself is to be replaced, the replacement may become more frequent and is burdensome, or, in the event the flat spring is subject to processing, it requires an increased number of steps and there is a threat of increasing the cost and making the spring constant unstable. Furthermore, considering making the diameter of actuator 100 itself small, the space for placing the flat spring decreases, and it becomes difficult to spread the stress by processing the flat spring.

By contrast with this, actuator 100 uses a coil spring as an elastic member to support movable body 110 in a movable fashion, and the coil spring is placed such that its axial core virtually matches the center of rotation when movable body 110 moves in resonance vibration.

Consequently, when movable body 110 moves in resonance vibration and moves in back-and-forth rotating motion, the stress which increases following the increase of the angle of rotation is produced uniformly in active coil part 133 of the coil spring. That is to say, unlike a case where a flat spring is used as an elastic material to support movable body 110 that moves in resonance vibration, it is possible to spread stress uniformly without applying special ingenuity to the shape in order to spread required stress. Consequently, as a member to support movable body 110 in a movable fashion, a structure provided that prevents stress from being concentrated on a location specific basis, that prevents the maximum stress value from increasing, and that therefore is robust against fatigue fracture.

Furthermore, the structure to support movable body 110 using a coil spring is likely to make possible miniaturization and can be made using a forming machine used in general, so that it is possible to lower the cost of making. Furthermore, the coil spring being elastic member 130 can practically absorb the load in the direction of thrust, so that it is possible to improve the anti-shock robustness of actuator 100.

The operation of actuator 100 will be described next.

Figure 6:
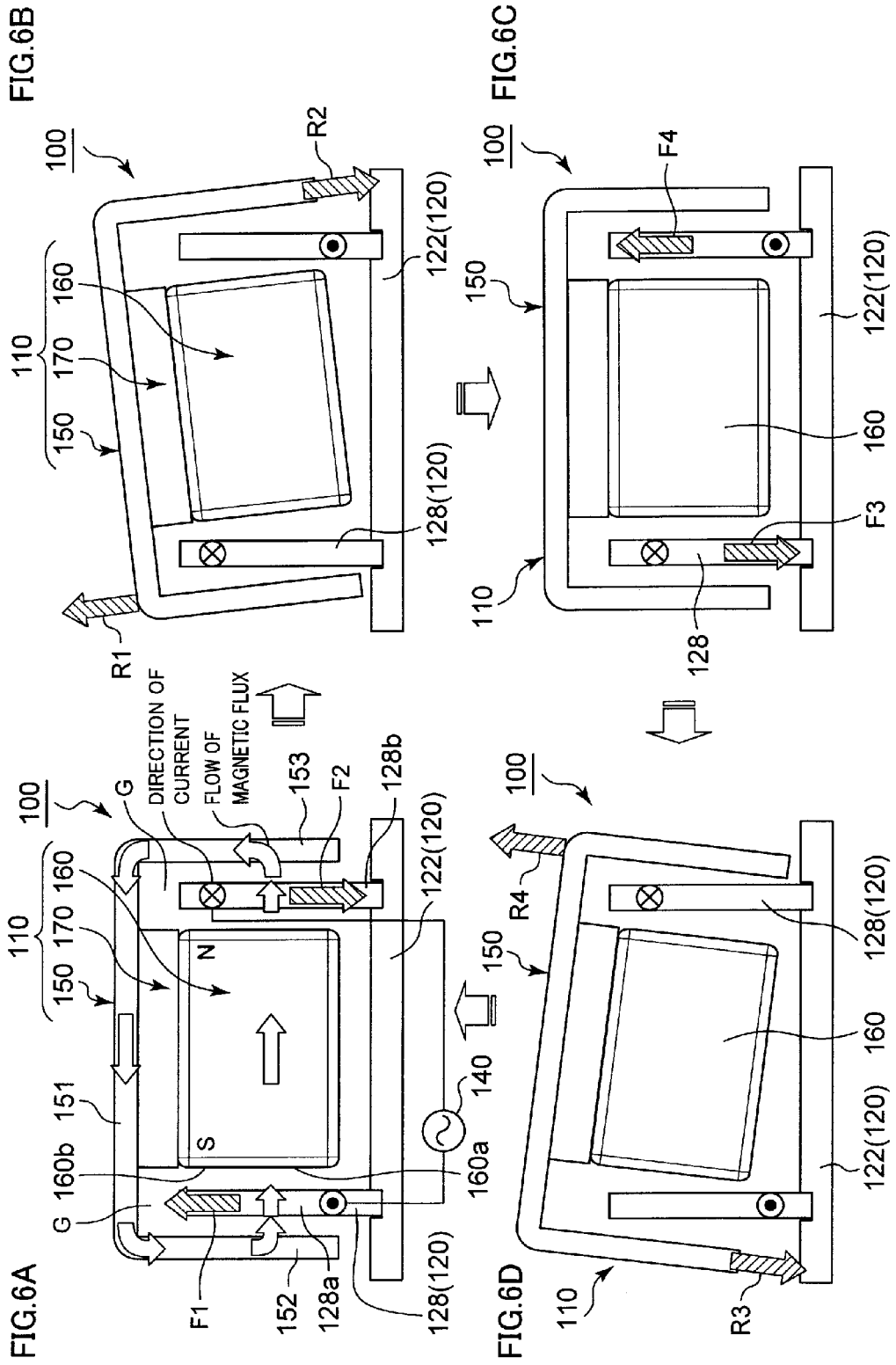
FIG. 6 is a schematic view for explaining operation of this actuator.

FIG. 6 is a schematic view for explaining the operation of actuator 100 according to the first embodiment. Although the flow of magnetic fluxes from magnet 160 is shown by outline arrows in FIG. 6A, the same flow applies to FIG. 6B to FIG. 6D, and illustration is omitted in FIG. 6B to FIG. 6D.

When an alternating current is supplied from alternating current supplying part 140 to coil 128, thrusts F1, F2, F3 and F4, represented by arrows in the drawing, are produced in coil 128, following Fleming's left hand rule. By this means, in movable body 110 that is attached to base plate 122 having coil 128, via support wall part 114, elastic member 130 and in a movable fashion, a rotating force about an axial center at the center of rotation is produced.

One operation cycle of actuator 100 will be described.

When a current flows in coil 128 in the direction shown in FIG. 6A (a current to flow in this direction will be hereinafter referred to as "forward current"), upward thrust F1 (directed toward outer yoke 150) is produced in part 128a of coil 128 opposing S-pole plane 160a of magnet 160. Meanwhile, in part 128b of coil 128 opposing N pole plane 160b of magnet 160, downward thrust F2 (directed toward base plate 112) is produced.

By this means, as shown in FIG. 1, FIG. 2 and FIG. 4, relative rotating force is produced in movable body 110 supported by support wall part 124 that is erected from base plate 122 having coil 122, guide shaft 125, elastic member 130 and support wall part 126. This relative rotating force places movable body 110 in the position shown in FIG. 6B.

In the state shown in FIG. 6B, actuator 100 produces reaction forces, designated by arrows R1 and R2, by the restoring force of elastic member 130. From the state shown in FIG. 6B to the state shown in FIG. 6D, a reverse current is supplied to coil 128 as compared with FIG. 6A. By this means, from the state shown in FIG. 6B to the state shown in FIG. 6C, movable body 110 rotates clockwise with respect to fixed body 120 by the reaction forces designated by arrows R1 and R2 and by the thrusts designated by arrows F3 and F4. From the state shown in FIG. 6C to the state shown in FIG. 6D, movable body 110 rotates clockwise with respect to fixed body 120 by the thrusts designated by arrows F3 and F4.

In the state shown in FIG. 6D, actuator 100 produces reaction forces, designated by arrows R3 and R4, by the restoring force of elastic member 130. From the state shown in FIG. 6D, passing the state shown in FIG. 6A, to the state shown in FIG. 6B, a forward current is supplied to coil 128. By this means, from the state shown in FIG. 6D to the state shown in FIG. 6A, movable body 110 rotates anticlockwise with respect to fixed body 120 by the reaction forces designated by arrows R3 and R4 and by the thrusts designated by arrows F1 and F2. From the state shown in FIG. 6A to the state shown in FIG. 6B, movable body 110 rotates anticlockwise with respect to fixed body 120 by the thrusts designated by arrows F1 and F2.

Next, the alternating current to be supplied in each state shown in FIG. 6 will be described briefly with reference to FIG. 7.

The alternating current to flow in coil 128 may be a pulse wave of frequency $f_0$ as shown in FIG. 7A or may be a sine wave of frequency $f_0$ as shown in FIG. 7B.

Figure 7:
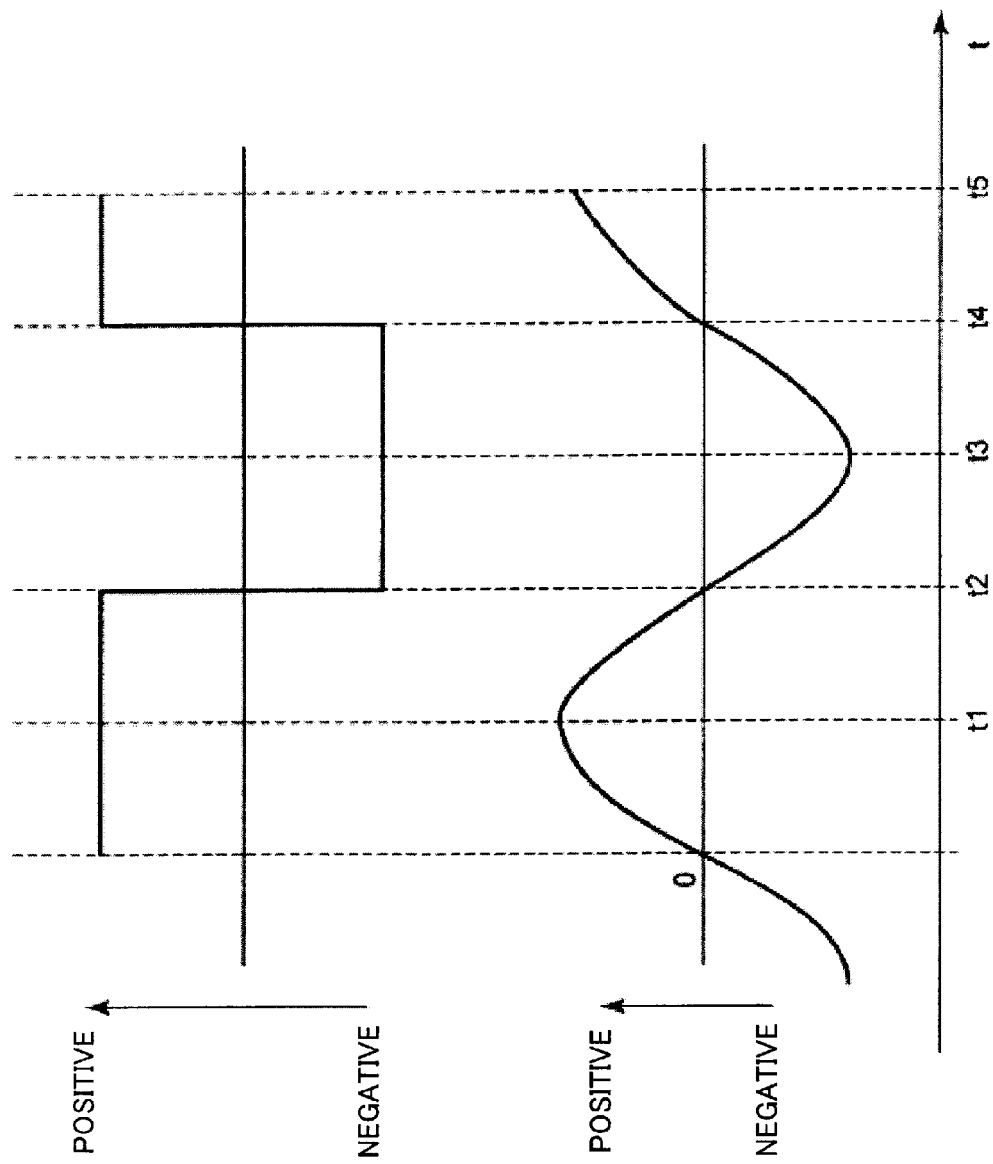
FIG. 7 shows a cycle of alternating current to be supplied to a coil in this actuator.

In the state of FIG. 6A, the forward current at time point t1 shown in FIG. 7 is supplied. In the state of FIG. 6B, the direction of the current is switched as shown at time point t2 in FIG. 7. In the state of FIG. 6C, the reverse current at time point t3 shown in FIG. 7 is supplied. Also, in the state of FIG. 6D, the direction of the current is switched as shown at time point t4 in FIG. 7, and, in the state of FIG. 6D, the forward current at time point t5 shown in FIG. 7 is supplied. This is one operation cycle, and, by repeating these operations, movable body 110 produces back-and-forth rotating vibration.

In actuator 100, movable body 110 produces back-and-forth rotating motion (that is, back-and-forth rotating vibration), and this back-and-forth rotating vibration is sent outside via output shaft 180. When a toothbrush part is coupled with output shaft 180 and a hair bundle part is provided to be perpendicular to the axial direction at the head of this toothbrush part, the toothbrush part moves in back-and-forth rotating vibration and makes possible rolling brushing.

By this means, actuator 100 satisfies equations 2 and 3 and is driven by a resonance phenomenon using the resonance frequency represented by equation 1. By this means, in actuator 100, the power to be consumed in a static state is only the loss due to load torque and the loss due to friction and the like, so that low power drive is possible—that is, it is possible to move movable body 110 in back-and-forth rotating vibration at low power consumption. As described above, with actuator 100 of the present embodiment, it is possible to realize back-and-forth rotating motion of an electric toothbrush or the like without using a drive transmitting mechanism apart from a drive source, and furthermore make possible back-and-forth rotating motion at low power consumption.

Furthermore, with this actuator 100, movable body 110 is driven using coil 128 which is a voice coil, so that magnetic attraction (detent force) is not produced, and therefore excellent controllability is provided. To be more specific, the position of movable body 110 while stopped is secured at the center location by the restoring force of elastic member 130, so that there is little power loss when the drive stops.

For the configuration of actuator 100, such a magnetic circuit is possible in which magnet 160 is replaced with a magnetic body of the same shape and in which two magnets are placed to turn differing magnetic pole planes to inner wall planes 152a and 153a of sidewall parts 152 and 153. In actuator 100, magnet 160 is attached to outer yoke 150, between sidewall parts 152 and 153, to turn different magnetic pole planes to sidewall parts 152 and 153, and is placed on the inner side of coil 128, thereby forming a magnetic circuit. By forming this magnetic circuit, compared to the configuration of making magnet 160 a magnetic body and attaching a plurality of magnets to the inner wall planes of sidewall parts 152 and 153, it is possible to reduce the number of magnets, improve the assembily and reduce the cost. An electric toothbrush having actuator 100 provides the same advantage, so that it is possible to miniaturize the electric toothbrush itself.

Second Embodiment

Figure 8:
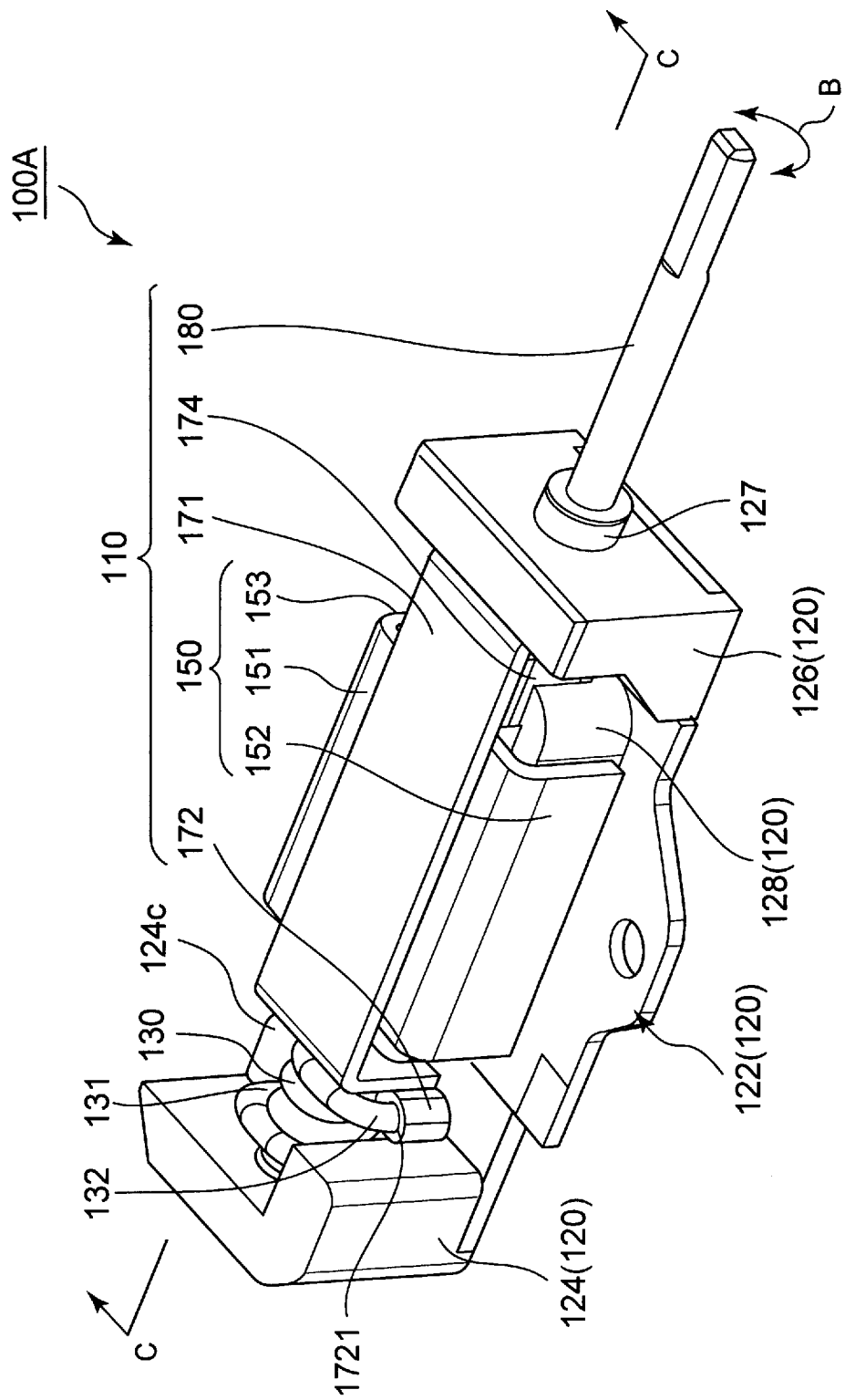
FIG. 8 is a perspective view showing an actuator according to a second embodiment of the present invention.
Figure 9:
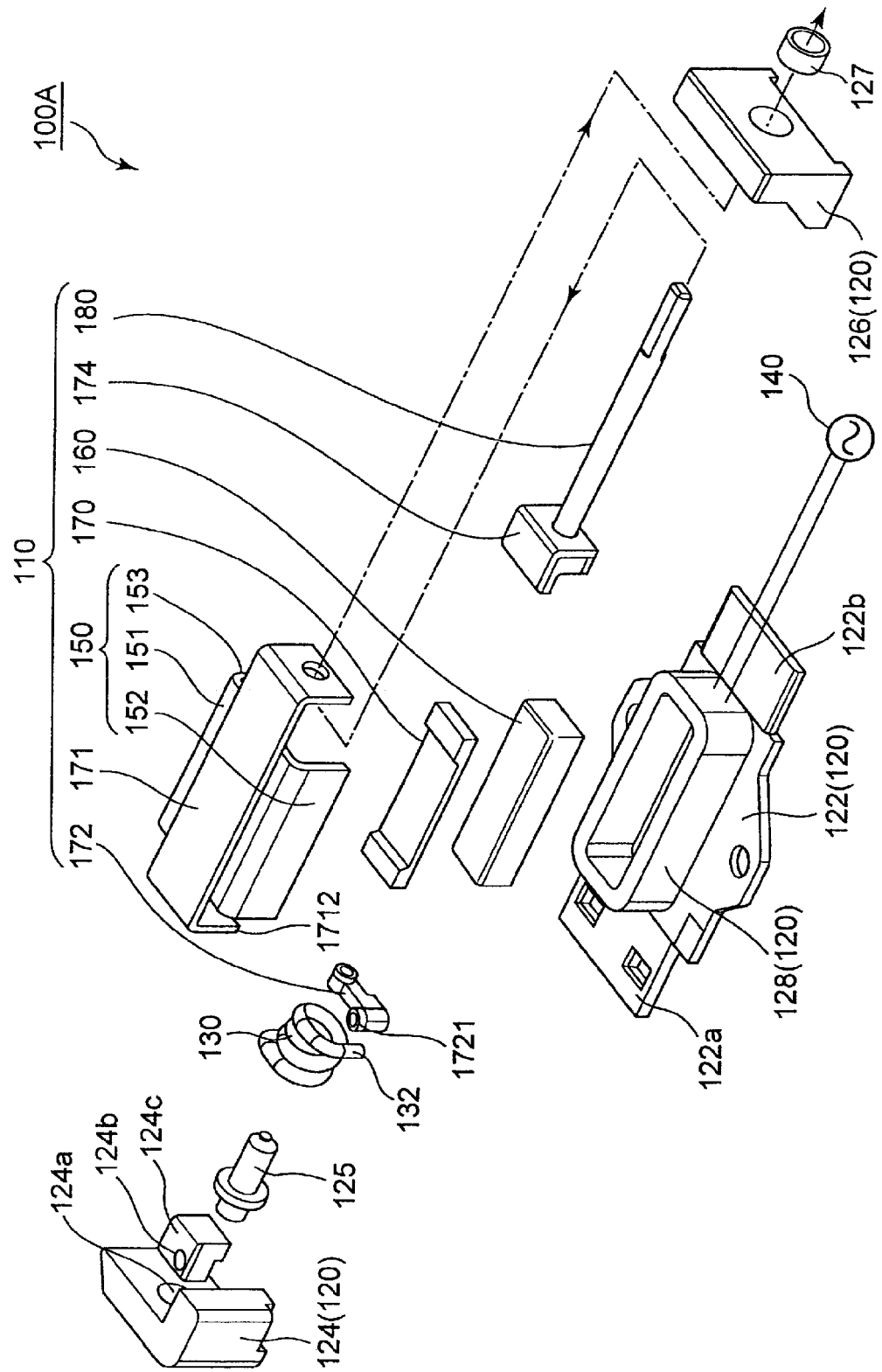
FIG. 9 is an exploded perspective view of this actuator.
Figure 10:
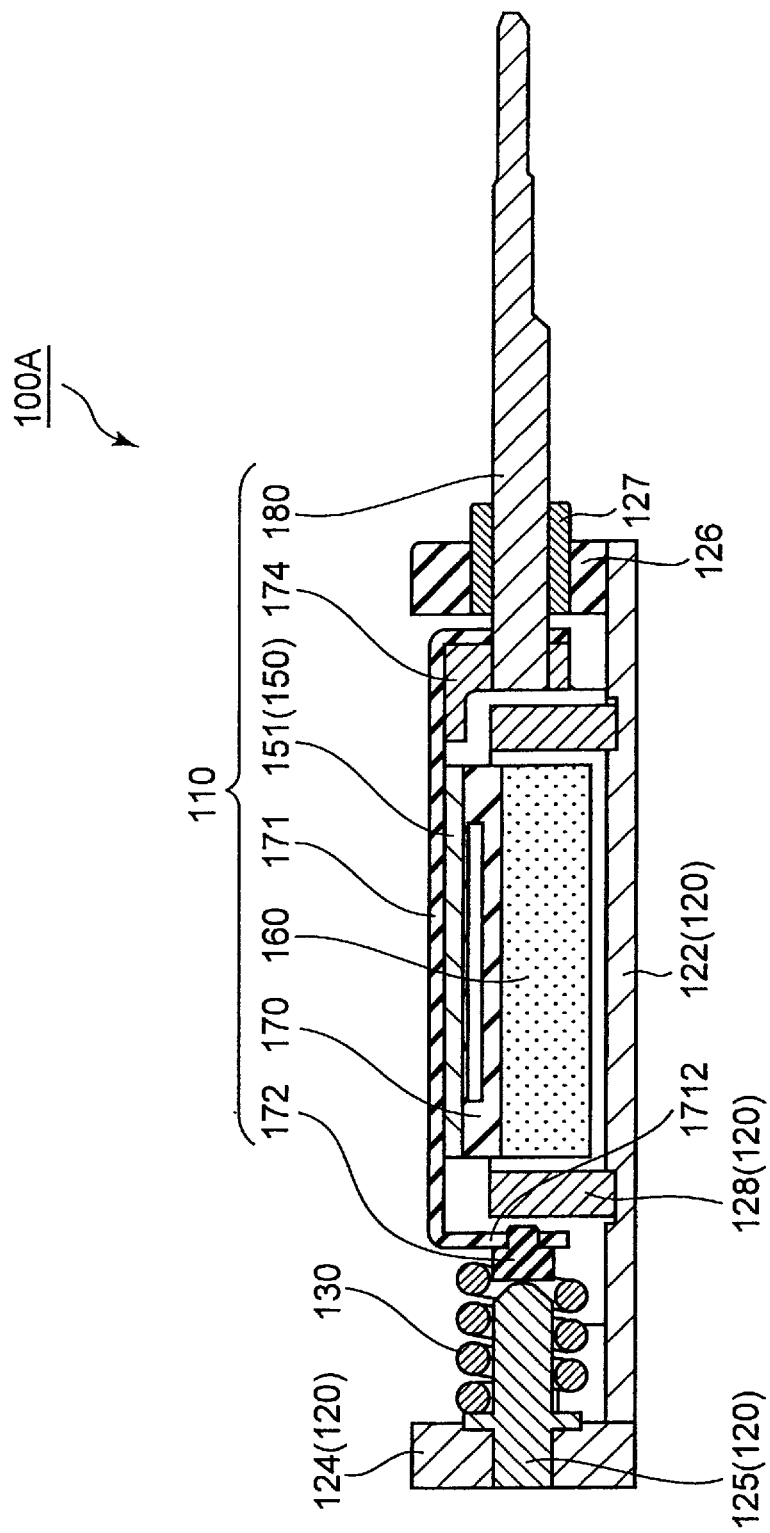
FIG. 10 is an arrow cross sectional view along line C-C in FIG. 8.

FIG. 8 is a perspective view showing actuator 100A according to a second embodiment of the present invention, and FIG. 9 is an exploded perspective view of this actuator 100A. FIG. 10 is an arrow cross sectional view along line C-C in FIG. 8. This actuator 100A basically has the same configuration as actuator 100 according to the first embodiment, shown in FIG. 1, and therefore parts in actuator 100A that are the same as in actuator 100 will be assigned the same reference numerals and codes as in actuator 100 and their explanations will be omitted.

Based upon actuator 100, actuator 100A has a configuration in which output shaft 180 of movable body 110 is axially supported, in a rotatable fashion, on fixed body 120, via bearing 127—that is, axially supported in a rotatable fashion coaxially with output shaft 180 in the configuration of actuator 100.

That is to say, based upon the configuration of actuator 100, actuator 100A attaches bearing 127 in opening part 126a in support wall part 126 in which output shaft 180 is inserted. Support wall part 126 supports output shaft 180 to be coaxial with guide shaft 125, in a rotatable fashion, via bearing 127. By this means, output shaft 180 transmits and outputs the movement/motion of movable body 110, and functions as a bearing to axially support movable body 110 on fixed body 120.

Consequently, the degree of freedom is improved with respct to rotation and in the axial direction, and, by improving the anti-shock robustness of actuator 100A itself, it is possible to move movable body 110 stably in back-and-forth rotating vibration.

Third Embodiment

Figure 11:
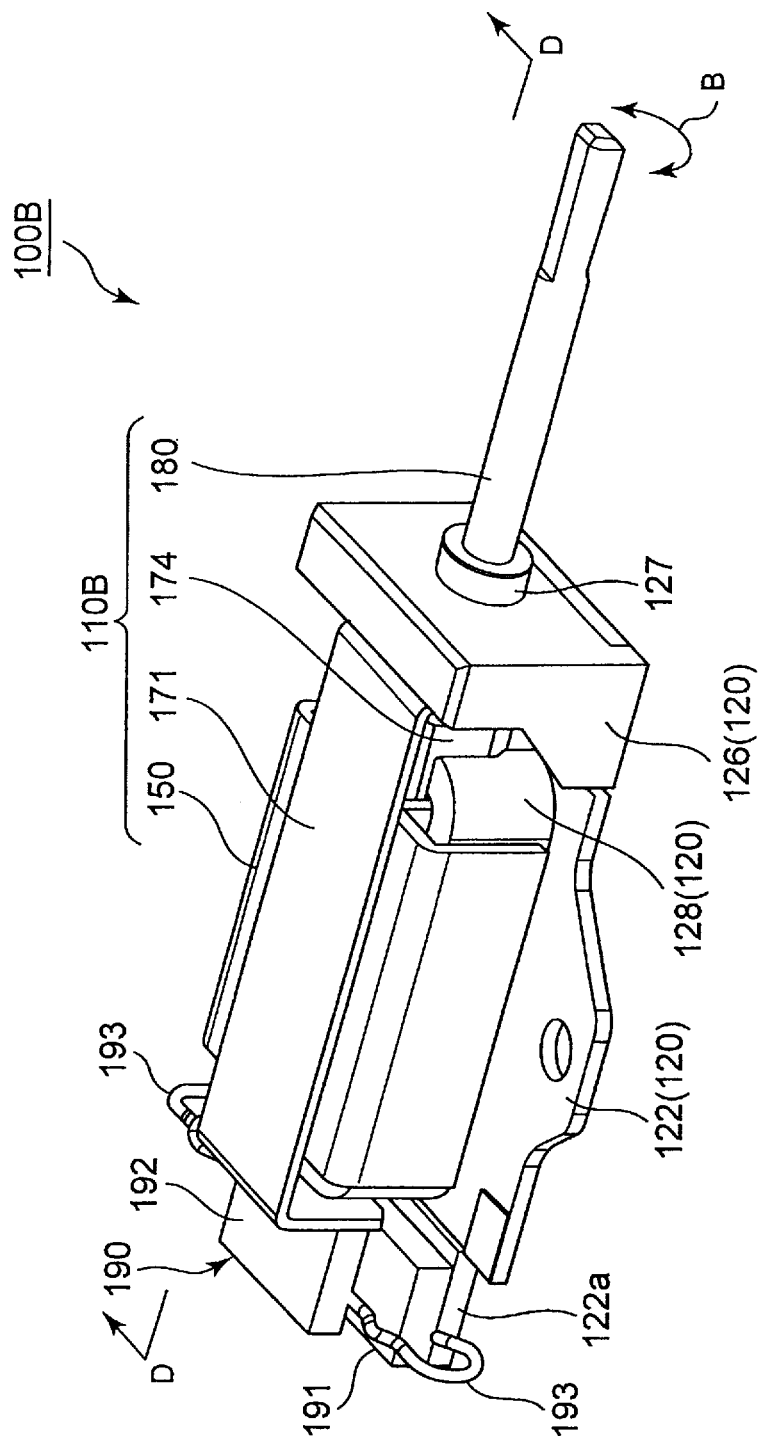
FIG. 11 is a perspective view showing an actuator according to a third embodiment of the present invention.
Figure 12:
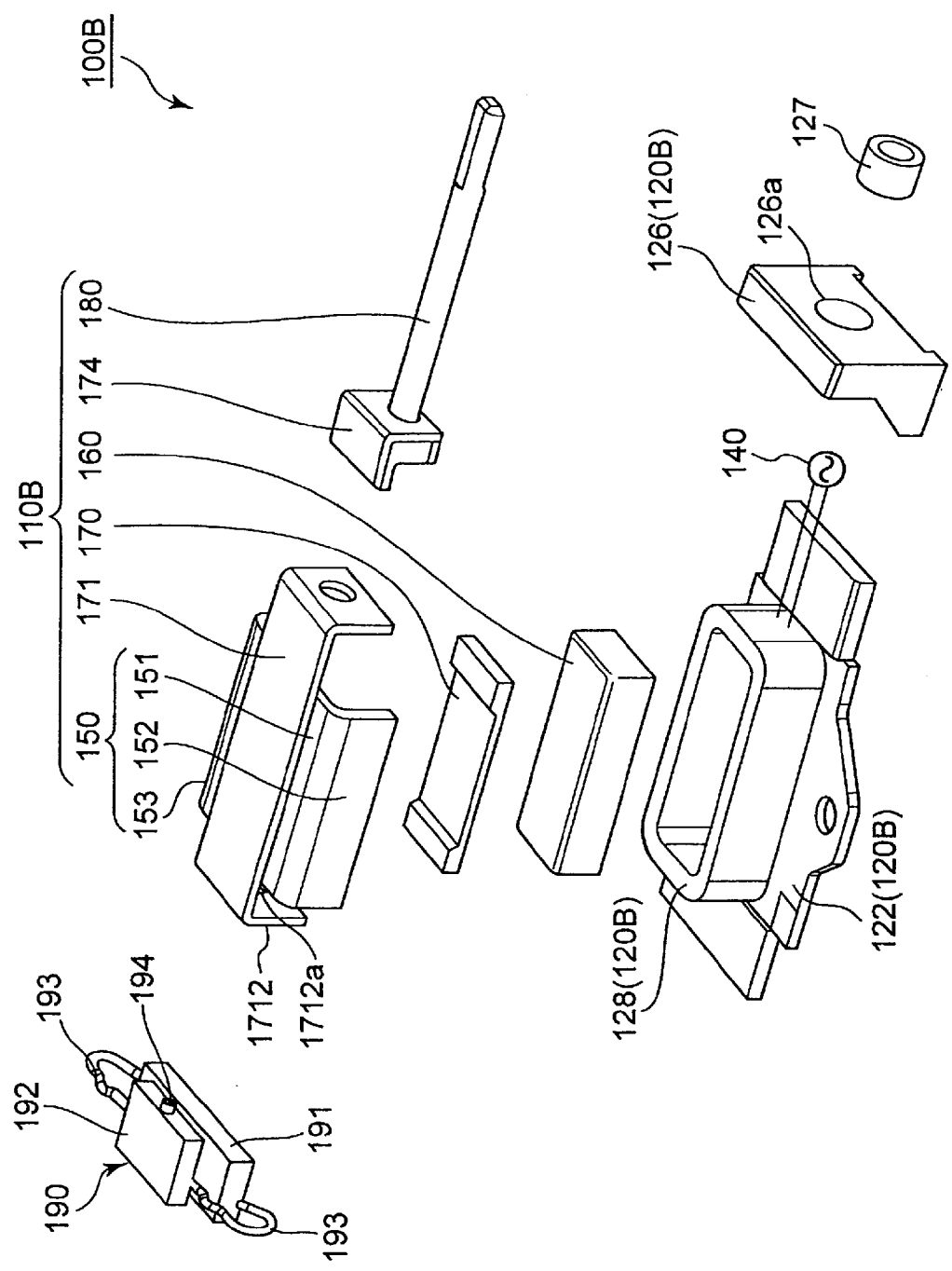
FIG. 12 is an exploded perspective view of this actuator.
Figure 13:
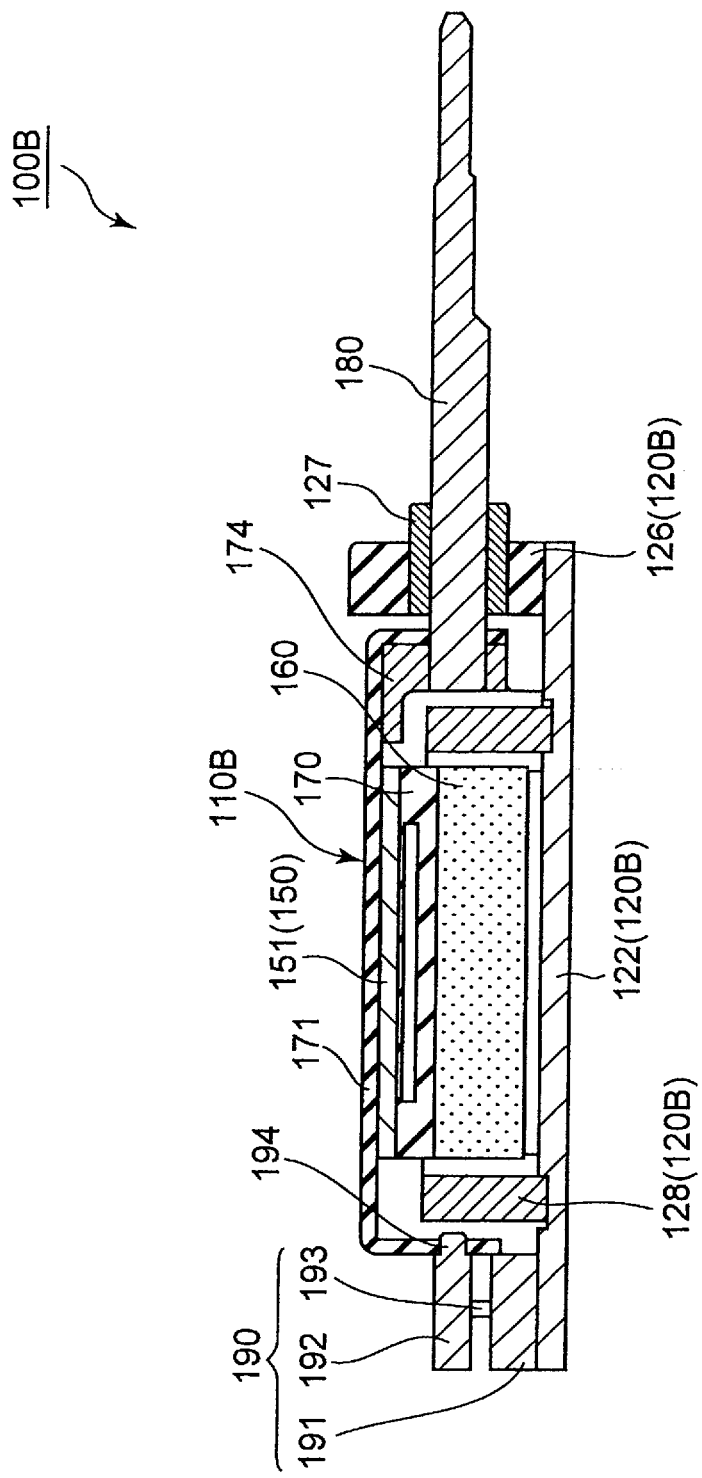
FIG. 13 is an arrow cross sectional view along line D-D in FIG. 11.

FIG. 11 is a perspective view showing actuator 100B according to a third embodiment of the present invention and FIG. 12 is an exploded perspective view of this actuator 100B. Also, FIG. 13 is an arrow cross sectional view along line D-D in FIG. 11. Actuator 100B basically has the same configuration as actuator 100 according to the first embodiment, shown in FIG. 1, and therefore parts in actuator 100B that are the same as in actuator 100 will be assigned the same reference numerals and codes as in actuator 100 and their explanations will be omitted.

Based upon the configuration of actuator 100A, actuator 100B uses wire-shaped spring body 190, instead of a coil spring being elastic member 130.

To be more specific, in the configuration of actuator 100A shown in FIG. 8 to FIG. 10, the coil spring being elastic member 130, support wall part 124, guide shaft 125 and joint part 172 are removed, and wire-shaped spring body 190 is attached.

Wire-shaped spring body 190 is provided in the rear end side of actuator 100B, between base plate 122 where coil 128 is erected in the center part on the surface, and yoke holder 171 of movable body 110B having magnet 160 that is placed a predetermined space apart in coil 128. Movable body 110B has a configuration removing joint part 172 from rear wall part 1712 of yoke holder 171 in mobile body 110 of actuator 100 or 100A.

Figure 14:
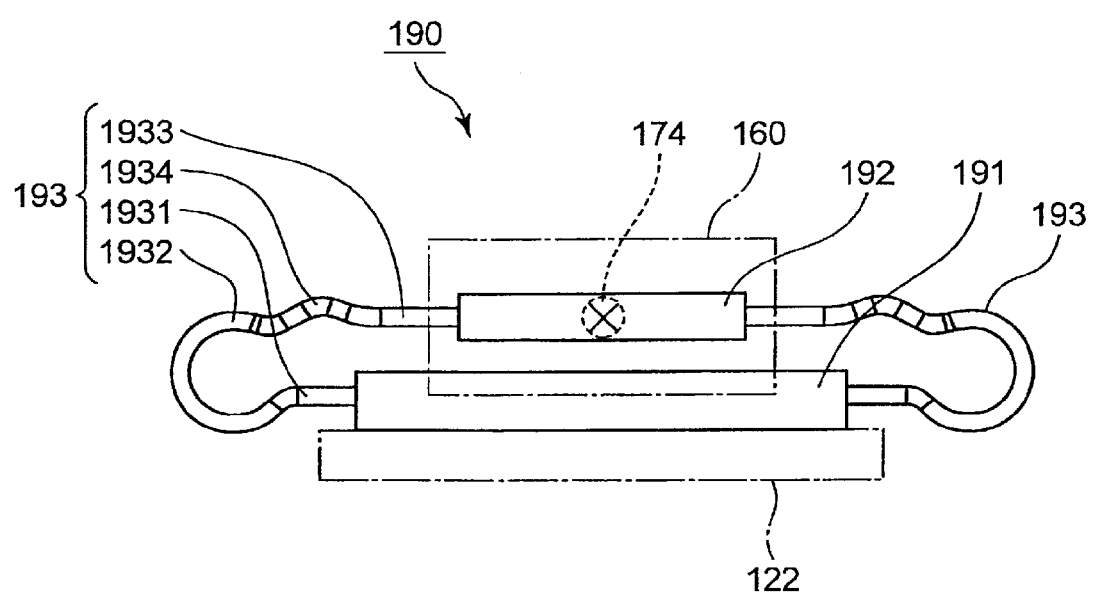
FIG. 14 is a rear view of a wire-shaped spring body of an actuator according to a third embodiment of the present invention.

FIG. 14 is a rear view of wire-shaped spring body 190 of actuator 100B according to a third embodiment of the present invention.

As shown in FIG. 11 to FIG. 14, wire-shaped spring body 190 has base plate fixing part 191 to be attached to base plate 122, yoke fixing part 192 to be fixed to yoke holder 171, and linear arm part 193 that is elastically deformable and that connects between base plate fixing part 191 and yoke fixing part 192.

As shown in FIG. 14, base plate fixing part 191 has a flat shape here and is attached to rear end part 122b of base plate 122. The front side of base plate fixing part 191 opposes rear wall part 1712 of yoke holder 171 of movable body 110B that is placed in a movable fashion.

Yoke fixing part 192 has a flat shape, placed above base plate fixing part 191 spaced apart, and placed in the front beyond base plate fixing part 191. Yoke fixing part 192 has projection part 194 that projects forward, in the center part of the front surface. As shown in FIG. 13, projection part 194 is inserted in opening part 1712a formed in rear wall part 1712 of yoke holder 171, thereby fixing yoke fixing part 192 to rear wall part 1712 of yoke holder 171. Projection part 194 is placed on the rotation axis of movable body 110B, and yoke fixing part 192 is fixed to yoke holder 171 in a bilateral position with respect to the center of rotation.

Arm parts 193 to project in horizontal directions are provided between both side parts of yoke fixing part 192 and both side parts of base plate fixing part 191.

Arm parts 193 are formed with a linear wire element that is elastically deformable (i.e. linear material). One end part of each arm part 193 is fixed to base plate 122 of fixed body 120B, and the other end is fixed to movable body 110B, thereby supporting movable body 110B on fixed body 120B to be capable of back-and-forth rotating motion about an axis along output shaft 180 (here, the axial center of output shaft 180).

Arm parts 193 are made by processing a linear material such that, when movable body 110B moves in back-and-forth rotating motion, the stress that is produced accompanying increasing distortion is spread or distributed over the entirety and is produced uniformly from the whole of arm parts 193.

Here, as shown in FIG. 14, in arm part 193, from the tip part of one side part 1931 that projects in directions (here, horizontal directions) to cross output shaft 180 from both sides of base plate fixing part 191, curved part 1932 to draw an upward curve is provide in a continuous fashion. Curved part 1934 is provided between the upper end of this curved part 1932 and opposite side part 1933, which is fixed in both side parts of yoke fixing part 192. Based on the degree of curve of these curved part 1932 and bent part, the stress that is produced in arm part 193 when movable body 110B is driven, is distributed uniformly. That is to say, the stress that applies to arm part 193 is distributed over the entirety, and the maximum stress value is made lower. By this means arm part 193 is not likely to be subject to fatigue fracture and does not have to be replaced frequently.

Furthermore, arm part 193 is formed by processing a linear material and therefore can be made by a forming machine, which is cost effective. Furthermore, since arm part 192 is formed by processing a linear material, it can be provided in small space, thereby improving the degree of freedom in terms of the design of actuator 100B itself. For example, compared to actuators 100 and 100A actuator 100B does not require a coil spring being elastic member 120, guide shaft 125 and joint part 172, so that it is possible to reduce the number of parts or and reduce the cost of parts.

Furthermore, unlike the configuration of actuators 100 and 100A, actuator 100B does not have to provide guide shaft 125 and joint part 172 before and after the coil spring being elastic member 130. By this means, compared to actuators 100 and 100A, actuator 100B is able to shorten its length in the direction of output shaft 180, which defines the axis of rotation, and allow further miniaturization.

Fourth Embodiment

Figure 15:
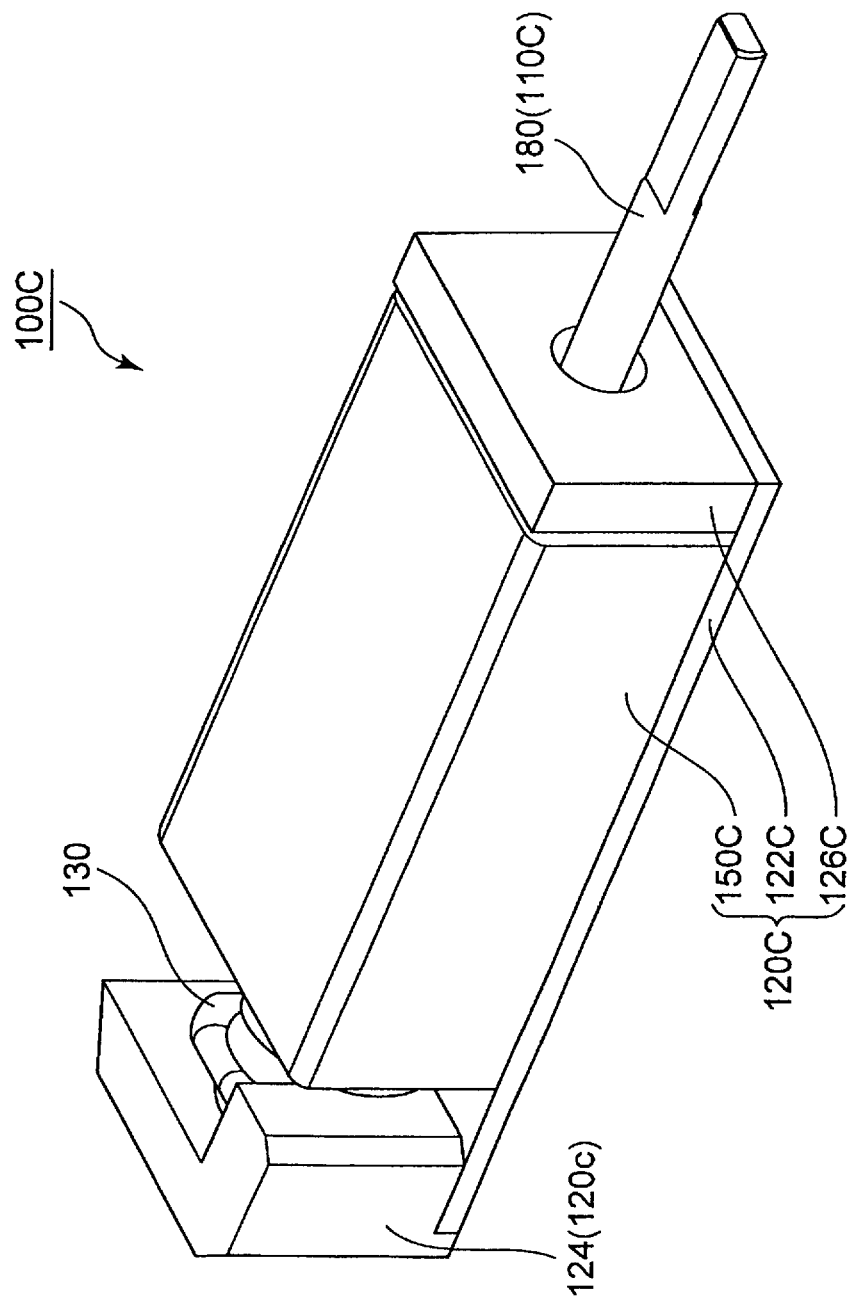
FIG. 15 is a perspective view showing an actuator according to a fourth embodiment of the present invention.
Figure 16:
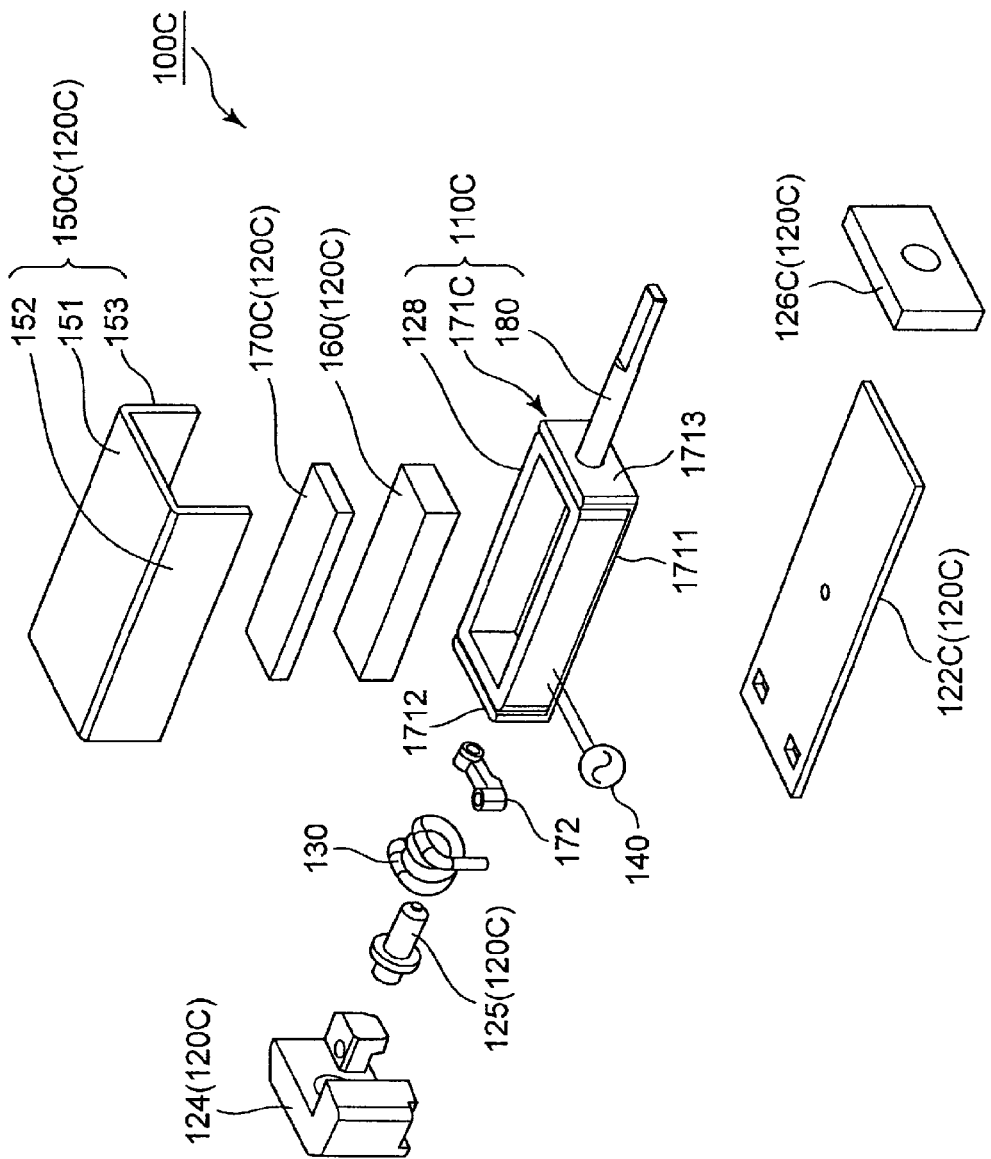
FIG. 16 is a principal-part exploded perspective view of this actuator.

FIG. 15 is a perspective view showing actuator 100C according to a fourth embodiment of the present invention, and FIG. 16 is a principal-part exploded perspective view of this actuator.

Actuator 100C according to this fourth embodiment has virtually the same magnetic circuit as in actuators 100 and 100A. By this means, the magnetic circuit of actuator 100 satisfies above equations 2 and 3, and, assuming that the inertia of movable body 110C is J and the spring constant in a twisting direction is $k_{sp}$, is driven by the resonance frequency calculated by above equation 1, with respect to fixed body 120C. Actuator 100C basically has the same configuration as actuator 100 according to the first embodiment, shown in FIG. 1, and therefore parts in actuator 100C that are the same as in actuator 100 will be assigned the same reference numerals and codes as in actuator 100 and their explanations will be omitted.

Actuator 100C shown in FIG. 15 and FIG. 16 has fixed body 120C, movable body 110C, coil spring 130 that supports movable body 110C on fixed body 120C in a movable fashion, and alternating current supplying part 140.

As shown in FIG. 16, with this actuator 100C, when movable body 110C that is supported in fixed body 120C via a coil spring (i.e. elastic member 130) moves, output shaft 180 of movable body 110C rotates in forward and backward directions (both directions of arrow B) in a predetermined angle range, and outputs back-and-forth rotating vibration outside.

As shown in FIG. 16, fixed body 120 has base plate 122C, support wall parts 124 and 126C, outer yoke 150C, and magnet 160 that is attached to outer yoke 150C via non-magnetic body (spacer) 170C.

In fixed body 120, base plate 122C forms a flat rectangular shape that is long in the direction in which output shaft 180 extends, and is formed of a non-magnetic body here. Above a center area on the surface of base plate 122C, coil 128 of movable body 110C is placed, and outer yoke 150C having a U-shaped cross section (including the shape of a letter U placed sideways) is attached to base plate 122C, to cover this coil 128.

Furthermore, support wall parts 124 and 126C are erected from edge parts of base plate 122C that are spaced apart in the long direction.

Support wall part 126C has opening part 126a in which output shaft 180 movable body 110C is inserted.

Also, support wall part 124 supports movable body 110C in a movable fashion via a coil spring, which is elastic member 130. That is to say, support wall parts 124 and 126C hold movable body 110C in a movable fashion via the coil spring being elastic member 130 in a state in which output shaft 180 is inserted in opening part 126a of support wall part 126C. In a normal state, movable body 110C is supported virtually horizontally (that is, virtually parallel to base plate 122C) by means of support wall parts 124 and 126C, elastic member 130, and so on. The structure for supporting movable body 110C on base plate 122C via elastic member 130 is the same as described above. That is to say, elastic member 130 (coil spring) is provided between guide shaft 125 attached to support wall part 124 that is erected in rear end part 122a of base plate 122C, and joint part 172 attached to the movable body 110C side. By this means, movable body 110 is supported to be able to move in back-and-forth rotating motion about output shaft 180 via elastic member 130.

Outer yoke 150C is placed between these support wall parts 124 and 126C to cover the main part of movable body 110C.

Outer yoke 150C has a cross section approximately in the shape of a letter U that is placed sideways, and is formed by bending a flat magnetic body. Outer yoke 150C has yoke center part 151 of a flat rectangular shape, and mutually opposing sidewall parts 152 and 153 that hang from the side parts of yoke center part 151. Here, between support wall parts 124 and 126, outer yoke 150C is placed from above to cover coil 128 and coil holder 171C of movable body 110C. Outer yoke 150C has its openings in the tip parts of sidewall parts 152 and 153 closed by base plate 122C, and, with base plate 122C and support wall parts 124 and 126C, forms a box shape to accommodate movable body 110C.

Outer yoke 150 constitutes a magnetic circuit with coil 128 of movable body 110C to be placed inside and magnet 160 that is attached in the back of yoke center part 151 of outer yoke 150.

Figure 17:
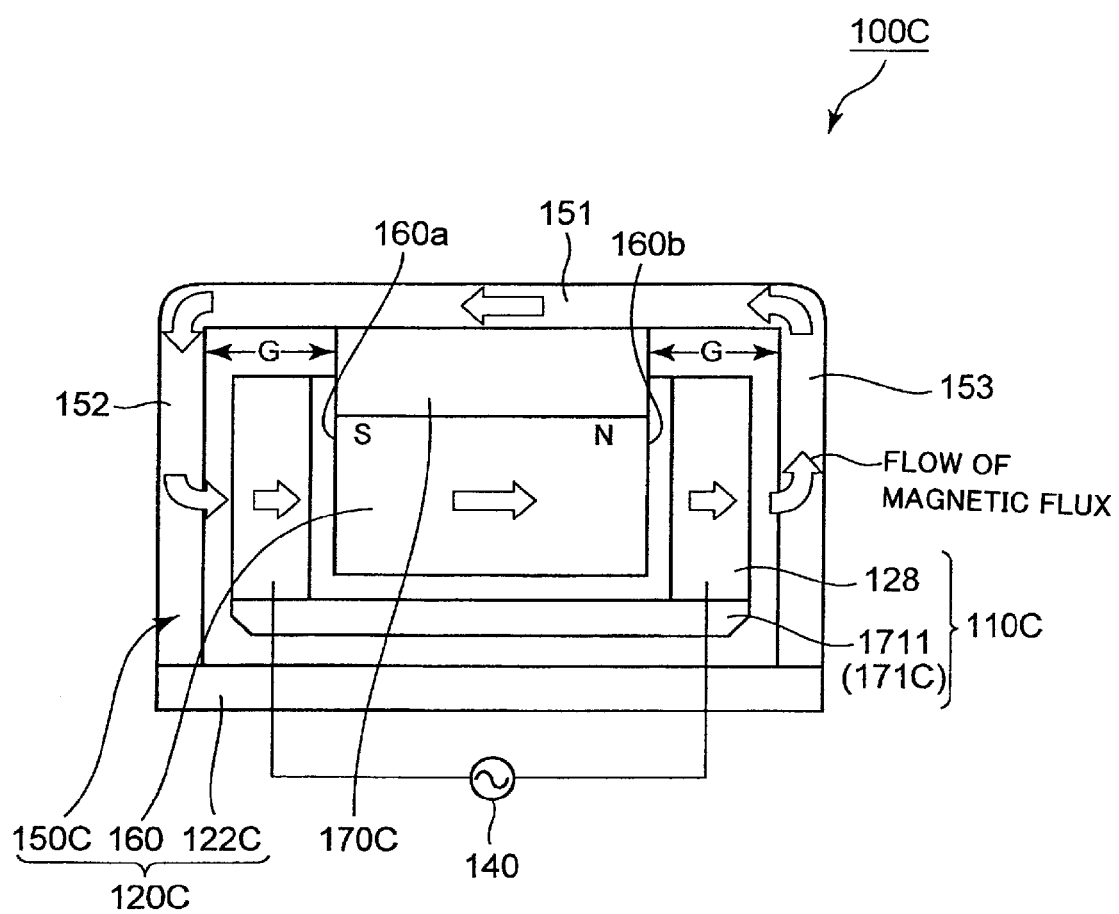
FIG. 17 is schematic cross-sectional view showing a principal-part configuration of this actuator.

FIG. 17 is a schematic cross-sectional view showing a principal-part configuration of actuator 100C according to the fourth embodiment.

As shown in FIG. 17, magnet (permanent magnet) 160 is placed in the center area on the back of yoke center part 151 of outer yoke 150C, via non-magnetic body 170C, such that air gaps G are formed between magnet 160 and opposing sidewall parts 152 and 153 of outer yoke 150C.

Magnet 160 is provided to hang from yoke center part 151, via non-magnetic body 170C, and different magnetic poles face the inner wall parts of sidewall parts 152 and 153.

That is to say, here, the S-pole end (S magnetic pole plane 160a) of magnet 160 faces the inner wall plane of sidewall part 152 of outer yoke 150C, and the N-pole side (N magnetic pole plane 160b) faces the inner wall plane of sidewall part 153 of outer yoke 150C.

Furthermore, magnet 160 is a cuboid having a length to match the length of the extension direction of outer yoke 150C, and is attached in yoke center part 151, via non-magnetic body 170C having the same outer shape, along the extension direction of yoke center part 151.

By this means, magnet 160 (see FIG. 16 and FIG. 17) has virtually the same length as the length of the long direction of outer yoke 150C, and is placed in yoke center part 151 in a state the inner wall planes of opposing sidewall parts 152 and 153 all face planes of different magnetic poles.

In air gaps G between magnet 160 and sidewall parts 152 and 153 of outer yoke 150C, coil 128 of movable body 110C is placed spaced apart from side wall planes (magnetic pole planes) 160a and 160b of magnet 160, inner wall planes of sidewall parts 152 and 153, and the back of yoke center part 151.

Coil 128, with coil holder 171C, output shaft 180, and joint part 172, constitutes movable body 110C.

To be more specific, in each air gap G, coil 128 is wound in a direction to be perpendicular to the direction in which magnet 160 and sidewall parts 152 and 153 oppose each other and surround the periphery of magnet 160. Similar to the first embodiment, from alternating current supplying part 140, an alternating current supply (AC voltage) is supplied to coil 128, as shown in FIG. 16 and FIG. 17.

This coil 128 is placed in coil holder 171C and held, and this coil holder 171C is supported by fixed body 120C via elastic member 130.

As shown in FIG. 16, this coil holder 171C is formed in the shape of a letter U placed sideways on a side view, and has bottom plate part 1711 on which coil 128 is placed, and front wall part 1713 and rear wall part 1712 that erect from edge parts of bottom plate part 1711 that are spaced apart along the long direction (that is, along the direction in which output shaft 180 extends).

This coil holder 171C is formed of a non-magnetic body.

In front wall part 1713, output shaft 180 is attached perpendicular, and, in rear wall part 1712, joint part 172 is attached. That is to say, output shaft 180 is placed approximately along the center of magnet 160, approximately parallel to varying magnetic pole planes 160a and 160b of magnet 160 (see FIG. 17).

Elastic member 130 supports movable body 110C between support wall part 124 and rear wall part 1712 such that movable body 110C is able to move in the front, back, left and right directions. Via this elastic member 130, in the area surrounded by base plate 122C and outer yoke 150C, movable body 110C is supported on fixed body 120C to be able to move in the twisting directions of magnet 160 and output shaft 180 about the axis of output shaft 180.

Incidentally, as shown in FIG. 15 and FIG. 16, output shaft 180 of movable body 110C is provided to project outward from support wall part 126C in the same direction as the direction of extension of outer yoke 150C. Incidentally, with actuator 100C, output shaft 180 is provided to project is a direction to be virtually perpendicular to the direction in which magnent 160 and sidewall parts 152 and 153 oppose each other.

Output shaft 180 is fixed in front wall part 1713 of coil holder 171C in this way, and, by this means, is attached to movable body 110C to be located on an axis to pass the center of gravity of movable body 110C. By this means output shaft 180 is able to move in back-and-forth rotating vibration with coil 128 and coil holder 171C constituting the main body of movable body 110C, and transmit this vibration outside.

When actuator 100C is used for an electric toothbrush, a toothbrush part is coaxially coupled with output shaft 180, and, at the head of this toothbrush part, a hair bundle part is provided to be perpendicular to the axial direction. By this means the toothbrush part moves in the same motion as output shaft 180, that is, moves in rolling motion, which is back-and-forth rotating vibration.

As shown in FIG. 17, with fixed body 120C and movable body 110C, outer yoke 150C, magnet 160 and coil 128 form a magnetic circuit.

Actuator 100C has a magnetic circuit where magnetic fluxes produced from magnet 160 (designated by outline arrows) pass an air gap where coil 128 is placed, sidewall part 153 of outer yoke 150C, yoke center part 151, sidewall part 152 and the opposite air gap, in order, and continue to the opposite pole of magnet 160.

Similar to movable body 110 of actuator 100, movable body 110C of this actuator 100C is supported by a spring mass system structure supported by fixed body 120C via elastic member 130. When an alternating current of the same frequency as resonance frequency $f_0$ of movable body 110C is supplied to coil 128 from alternating current supplying part 140, movable body 110C is driven in a resonant state efficiently. The back-and-forth rotating vibration that is produced then is transmitted from output shaft 180 to the outside.

Actuator 100C is driven based on the equation of motion represented by equation 2 below and based on the circuit equation represented by equation 3 below. Consequently, the inertia moment, rotation angle, torque constant, current, spring constant, attenuation coefficient, and load torque in actuator 100C can be changed as adequate in a range to satisfy equation 2, and the voltage, resistance, inductance, and counter electromotive force multiplier can be changed as adequate in a range to satisfy equation 3.

Next, the operations of actuator 100C will be described in detail.

FIG. 18 is a schematic view for explaining operation of actuator 100C according to the fourth embodiment. Although the flow of magnetic fluxes from magnet 160 is shown by outline arrows in FIG. 18A, the same flow applies to FIG. 18B to FIG. 18D, and illustration is omitted in FIG. 18B to FIG. 18D. Also, although FIG. 18A shows alternating current supplying part 140 that supplies an AC voltage to coil 128, the same applies to FIG. 18B to FIG. 18D, and illustration is omitted in FIG. 18B to FIG. 18D.

When an alternating current is supplied from alternating current supplying part 140 to coil 128, thrusts F1, F2, F3 and F4 in the drawing are produced in coil 128, following Fleming's left hand rule. By this means, in movable body 110C that is attached to fixed body 120C in a movable fashion, a rotating force about an axial center at the center of rotation is produced.

One operation cycle of actuator 100C will be described.

When a current flows in coil 128 in the direction shown in FIG. 18A (a current to flow in this direction will be hereinafter referred to as "forward current"), upward thrust F1 (directed toward outer yoke 150C) is produced in part 128b of coil 128 opposing N-pole plane 160b of magnet 160. Meanwhile, in part 128a of coil 128 opposing S pole plane 160a of magnet 160, downward thrust F2 (directed toward base plate 122C) is produced.

By this means, a rotating force is produced in movable body 110C that has coil 128 and that is supported by support wall parts 124 and 126C that erect from base plate 122C of fixed body 120C (see FIG. 16 and FIG. 17), via elastic member 130. Movable body 110C moves anticlockwise to assume the position shown in FIG. 18B by thrusts F1 and F2 of coil 128.

In the state shown in FIG. 18B, actuator 100C produces reaction forces, designated by arrows R1 and R2, by the restoring force of elastic member 130 (see FIG. 15 and FIG. 16). From the state shown in FIG. 18B to the state shown in FIG. 18D, a reverse current is supplied to coil 128 as compared with FIG. 18A. By this means, from the state shown in FIG. 18B to the state shown in FIG. 18C, movable body 110C rotates clockwise with respect to fixed body 120C by the reaction forces designated by arrows R1 and R2 and by the thrusts designated by arrows F3 and F4. From the state shown in FIG. 18C to the state shown in FIG. 18D, movable body 110C rotates clockwise with respect to fixed body 120C by the thrusts designated by arrows F3 and F4.

In the state shown in FIG. 18D, actuator 100C produces reaction forces, designated by arrows R3 and R4, by the restoring force of elastic member 130. From the state shown in FIG. 18D to the state shown in FIG. 18A, a forward current is supplied to coil 128. By this means, from the state shown in FIG. 18D to the state shown in FIG. 18A, movable body 110C rotates anticlockwise with respect to fixed body 120C by the reaction forces designated by arrows R3 and R4 and by the thrusts designated by arrows F1 and F2.

From the state shown in FIG. 18A to the state shown in FIG. 18B, movable body 110C rotates anticlockwise with respect to fixed body 120C by the thrusts designated by arrows F1 and F2. Although movable body 110C operates in back-and-forth rotating vibration about magnet 160, but movable body 110C is also able to operate in the same way as shown in FIG. 18 by thrusts F1 to F4, without using the reaction force of elastic member 130.

The alternating current to be supplied to coil 128 in each state shown in FIG. 18 may be a pulse wave of frequency $f_0$ as shown in FIG. 7A or may be a sine wave of frequency $f_0$ as shown in FIG. 7B.

The cycle of alternating current supplied from alternating current supplying part 140 to coil 128 of movable body 110C in the actuator according to the present embodiment is the same as in actuator 100.

In the state of FIG. 18A, the forward current at time point t1 shown in FIG. 7 is supplied. In the state of FIG. 18B, the direction of the current is switched as shown at time point t2 in FIG. 7. In the state of FIG. 18C, the reverse current at time point t3 shown in FIG. 7 is supplied. Also, in the state of FIG. 18D, the direction of the current is switched as shown at time point t4 in FIG. 7, and, in the state of FIG. 18D, the forward current at time point t5 shown in FIG. 7 is supplied. This is one operation cycle, and, by repeating these operations, movable body 110C produces back-and-forth rotating vibration.

Actuator 100C uses a coil spring for elastic member 130 to support movable body 110C to be able to move in back-and-forth rotating motion. That is to say, unlike a case where a flat spring is used as an elastic member to support movable body 110 that moves in resonance vibration, it is possible to spread stress uniformly without applying special ingenuity to the shape in order to spread required stress. Consequently, as a member to support movable body 110 in a movable fashion, a structure is provided that prevents stress from being concentrated on a location specific basis, that prevents the maximum stress value from increasing, and that therefore is robust against fatigue fracture. Furthermore, this structure is likely to make possible miniaturization and can be made using a forming machine used in general, so that it is possible to lower the cost of making. Furthermore, given that a coil spring can practically absorb the load in the direction of thrust, it is possible to improve the anti-shock robustness of actuator 100 itself.

Actuator 100C configured thus has the same working effects as actuator 100.

In addition, movable body 110C is formed with coil 128 and coil holder 171C, without outer yoke 150C. Consequently, the scale of the inertia moment of movable body 110C does not depend on the outer shape and is determined based upon the shape of coil 128. Coil 128 is placed in a position on the inner side outer yoke 150 and therefore is unlikely to be a factor to increase the inertia. The increase of inertia moment due to change of the outer shape of actuator 100C is reduced, so that constraints are removed in terms of design, and it is therefore possible to improve the freedom of design with respct to actuator 100C itself.

An electric toothbrush having actuator 100C provides the same advantage, so that it is possible to miniaturize the electric toothbrush itself.

Figure 20:
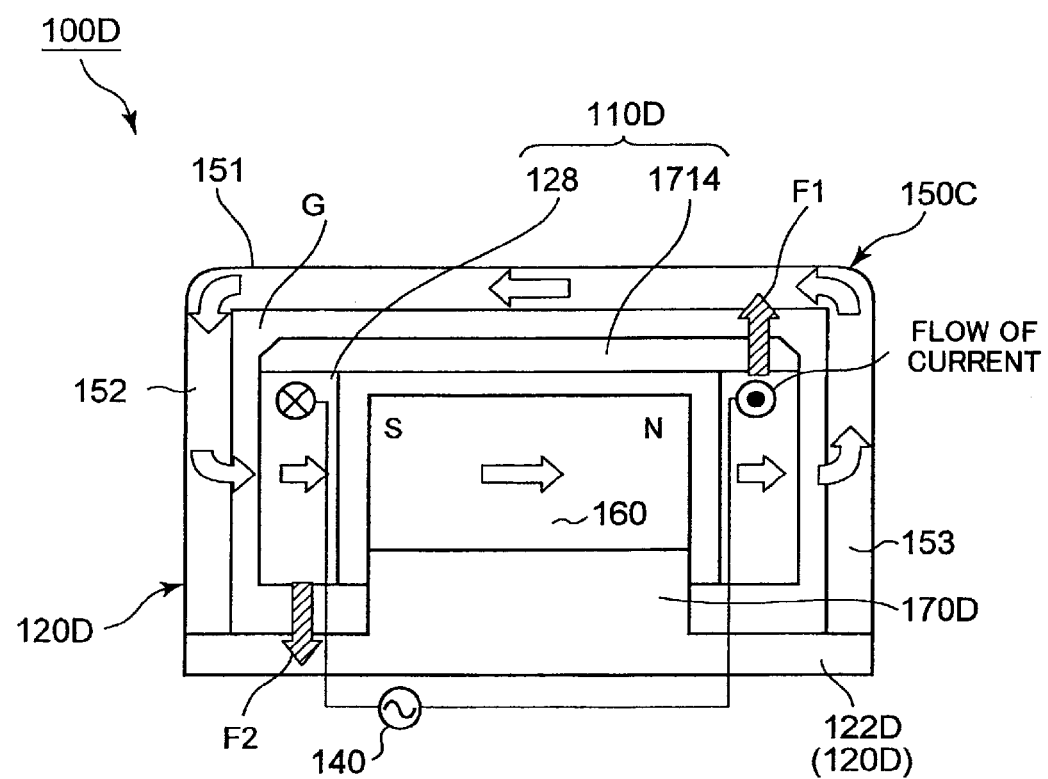
FIG. 20 is a schematic cross-sectional view showing configurations of a movable body and fixed body of this actuator.

In the configuration of actuator 100C, base plate 122C may be formed by a magnetic body. With this configuration, actuator 100C forms two paths for magnetic fluxes by magnet 160 in fixed body 120C. That is to say, as shown in FIG. 20, in the magnetic circuit of actuator 100C, magnetic fluxes that are produced from magnet 160 pass an air gap where coil 128 is placed, and, through sidewall part 153 of outer yoke 150C and yoke center part 151, arrive at sidewall part 152. Next, from sidewall part 153 of outer yoke 150C, the magnetic fluxes pass base plate 112C on the opposite side from yoke center part 151, and then arrive at sidewall part 152. Magnetic fluxes pass sidewall part 152 and the opposite air gap from the above air gap, in order, and continue to the opposite pole of magnet 160. By this means, the magnetic saturation in the magnetic circuit is reduced, so that it is possible to increase the thrust of movable body 110C that is produced when an AC voltage is supplied from alternating current supplying part 140 to coil 128. Furthermore, in the event base plate 122C in actuator 100C is made a magnetic body, the outer periphery part of fixed body 120C accommodating movable body 110C in a movable fashion—that is, a magnetic circuit including magnetic 160—is formed by outer yoke 150C, which is a magnetic body, and base plate 122C, which is also a magnetic body. That is to say, by forming the outer surface of actuator 100C using a magnet body, in actuator 100C, it is possible to prevent magnetic fluxes from leaking from the magnetic circuit including base plate 112C, outer yoke 150C, magnet 160 and coil 128.

Fifth Embodiment

Figure 19:
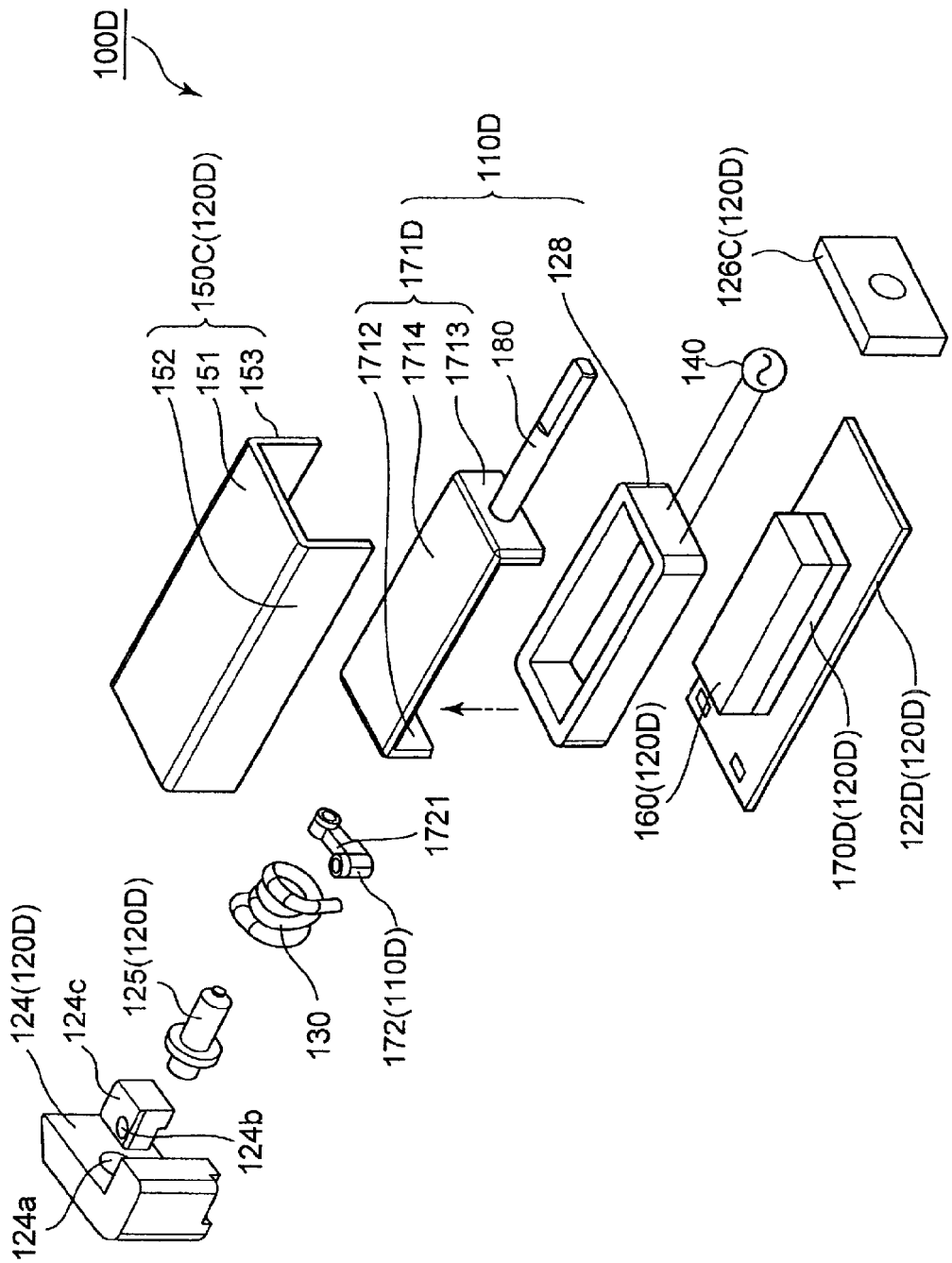
FIG. 19 is exploded perspective view showing a configuration of an actuator according to a fifth embodiment of the present invention.

FIG. 19 is exploded perspective view showing a configuration of actuator 100D according to a fifth embodiment of the present invention. FIG. 20 is schematic cross-sectional view showing configurations of movable body 110D and fixed body 120D of this actuator 100D. This actuator 100D basically has the same configuration as actuator 100 according to the fourth embodiment, shown in FIG. 15 and FIG. 16, and therefore parts in actuator 100D that are the same as in actuator 100 will be assigned the same reference numerals and codes as in actuator 100 and their explanations will be omitted.

Base upon the configuration of actuator 100C, actuator 100D of the fifth embodiment is configured by, maintaining the magnetic circuit configuration, removing magnet 160 from outer yoke 150C and fixing it on the base plate 122D side via a non-magnetic body (spacer). In addition, movable body 110D is formed by turning movable body 110C having coil 128 in actuator 100C upside down and attaching this movable body 110D to fixed body 120D via elastic member 130 so as to be able to move in back-and-forth rotating vibration in twisting directions.

To be more specific, actuator 100D has fixed body 120D, movable body 110D, elastic member 130 that supports movable body 110D on fixed body 120D to be able to move in twisting directions about output shaft 180 of movable body 110D, and alternating current supplying part 140.

As shown in FIG. 19 and FIG. 20, fixed body 120D has base plate 122D, magnet 160 that is placed on base plate 122D via projection part 170D of a non-magnetic body (spacer), and U-shaped outer yoke 150C that is attached to base plate 122D to cover magnet 160. Furthermore, fixed body 120D has support wall parts 124 and 126C that are spaced apart between the front side and rear side of movable body 110D. Movable body 110D connects joint part 172 to elastic member 130 that is attached outwardly to guide shaft 125 of support wall part 124 and inserts output shaft 180 in opening part 126a of support wall part 126, and, by this means, is supported on fixed body 120D to be capable of back-and-forth rotating motion.

As shown in FIG. 20, in fixed body 120D, base plate 122D of a flat rectangular shape is formed by a non-magnetic body, and magnet 160 is attached via non-magnetic projection part 170D that is projected in the center part on the surface to project upward.

Magnet 160 is placed on non-magnetic projection part 170B such that air gaps are formed between its differing magnetic pole planes and opposing sidewall parts 152 and 153 of outer yoke 150C.

Like magnet 160 of the above embodiments, the magnetic pole planes of magnet 160 are spaced apart in a direction perpendicular to output shaft 180 and oppose sidewall parts 152 and 153 of outer yoke 150C.

Projection part 170D is formed on base plate 122D integrally and has the same outer shape as magnet 160. Here, projection part 170D is a cuboid to extend, with magnet 160, in the long direction of base plate 122D. Projection part 170D places magnet 160 apart from base plate 122D, thereby securing an area to allow coil 128 of movable body 110D located in the surroundings of magnet 160 to move in back-and-forth rotation about magnet 160.

Thus, movable body 110D is placed on fixed body 120D such that coil 128 and upper plane part 1714 of coil holder 171D are placed over magnet 160 attached on projection part 170D projecting from base plate 122D via an air gap.

Movable body 110D is placed in an air gap formed between opposing inner wall planes of outer yoke 150C and magnet 160, and is formed with coil 138 that surrounds magnet 160, and coil holder 171D that holds coil 128.

In coil holder 171D where front wall part 1713 and rear wall part 1712 hang from edge parts that are spaced part in the log direction, coil 128 is attached on the back of upper plane part 1714.

Coil holder 171D has joint part 172 that is attached to rear wall part 1712, and, via this joint part 172, opposite end part 132 of elastic member 130, provided between coil holder 171D and support wall part 124 of fixed body 120D is fixed. Coil holder 124B is attached to support wall parts 114 and 116 of fixed body 120B, via elastic member 130, to be able to move in twisting directions about shafts 125 and 126 provided perpendicular to the axial direction of coil 170. By this means, movable body 110D is attached to fixed body 120D to be able to move in twisting directions about output shaft 180.

Similar to actuators 100 and 100C, an alternating current having approximately the same frequency as a resonance frequency is supplied to coil 128 from alternating current supplying part 140 that supplies an AC voltage. By this means, movable body 110D, supported in fixed body 120C by means of elastic member 130 to be able to move in twisting directions of output shaft 180, moves in back-and-forth rotating vibration by the thrust by coil 128 in fixed body 120D.

As shown in FIG. 20, actuator 100D has a magnetic circuit where magnetic fluxes produced from magnet 160 (designated by outline arrows) pass air gap G where coil 128 is placed, sidewall part 153 of outer yoke 150C, yoke center part 151, sidewall part 152 and the opposite air gap, in order, and continue to the opposite pole of magnet 160. In FIG. 20, the flow of magnetic fluxes in the magnetic circuit of actuator 100D is shown by outline arrows.

When an alternating current is supplied from alternating current supplying part 140 to coil 128 in actuator 100D (see FIG. 7) as in the case of actuator 100C, following Fleming's left hand rule, the thrusts designated by arrows F1 and F2 in the drawing and reverse thrusts to these thrusts designated F1 and F2 are produced alternately. By this means, a rotating force about an axial center being output shaft 180, which is the center of rotation, is produced in coil 128, and movable body 110D repeats the same operation (see FIG. 10) as coil 128 of actuator 100C shown in FIG. 18, and produces back-and-forth rotating vibration.

Furthermore, although actuator 100D of this embodiment places magnet 160 differently compared to actuator 100C, the magnetic circuit configuration is the same and the same effect as actuators 100 and 100C described above can be provided. In particular, with actuator 100B, it is possible to achieve back-and-forth rotating motion of an electric toothbrush or the like without using a drive transmitting mechanism apart from a drive source.

Furthermore, since actuator 100D directly places magnet 160 on projection part 170B that is formed on non-magnetic base plate 122D integrally, so that, compared to actuator 100C, it is not necessary to use a separate non-magnetic body and it is therefore possible to reduce the number of parts and make actuator 100D more cost effective.

Furthermore, upon assembly, magnet 160 is placed on projection part 170D that projects from the surface of flat base plate 122D, so that, compared to the case of placing magnet 160 in the denting interior of U-shaped outer yoke 150, it is possible to perform positioning and assembling operations easily.

In the configuration of actuator 100D, it is equally possible to form base plate 122D by a different magnetic body from that of projection part 170D and provide projection part 170D in base plate 122D of this magnetic body. With this configuration, compared to actuator 100, actuator 100A forms two paths for magnetic fluxes by magnetic 150 in fixed body 120. That is to say, as shown in FIG. 7, in the magnetic circuit of actuator 100D, magnetic fluxes (shown by outline arrows) that are produced from magnet 160 pass an air gap where coil 128 is placed, pass from sidewall part 153 of outer yoke 150 to yoke center part 151, and, in addition, pass from sidewall part 153 to base plate 122D on the opposite side of yoke center part 151, and then arrive at sidewall part 152. Magnetic fluxes passing this sidewall part 152 then pass the opposite air gap and continue to the opposite pole of magnet 160. By this means, it is possible to achieve the same working effect as in the case where base plate 122C is made a magnetic body in the fourth embodiment.

Sixth Embodiment

Figure 21:
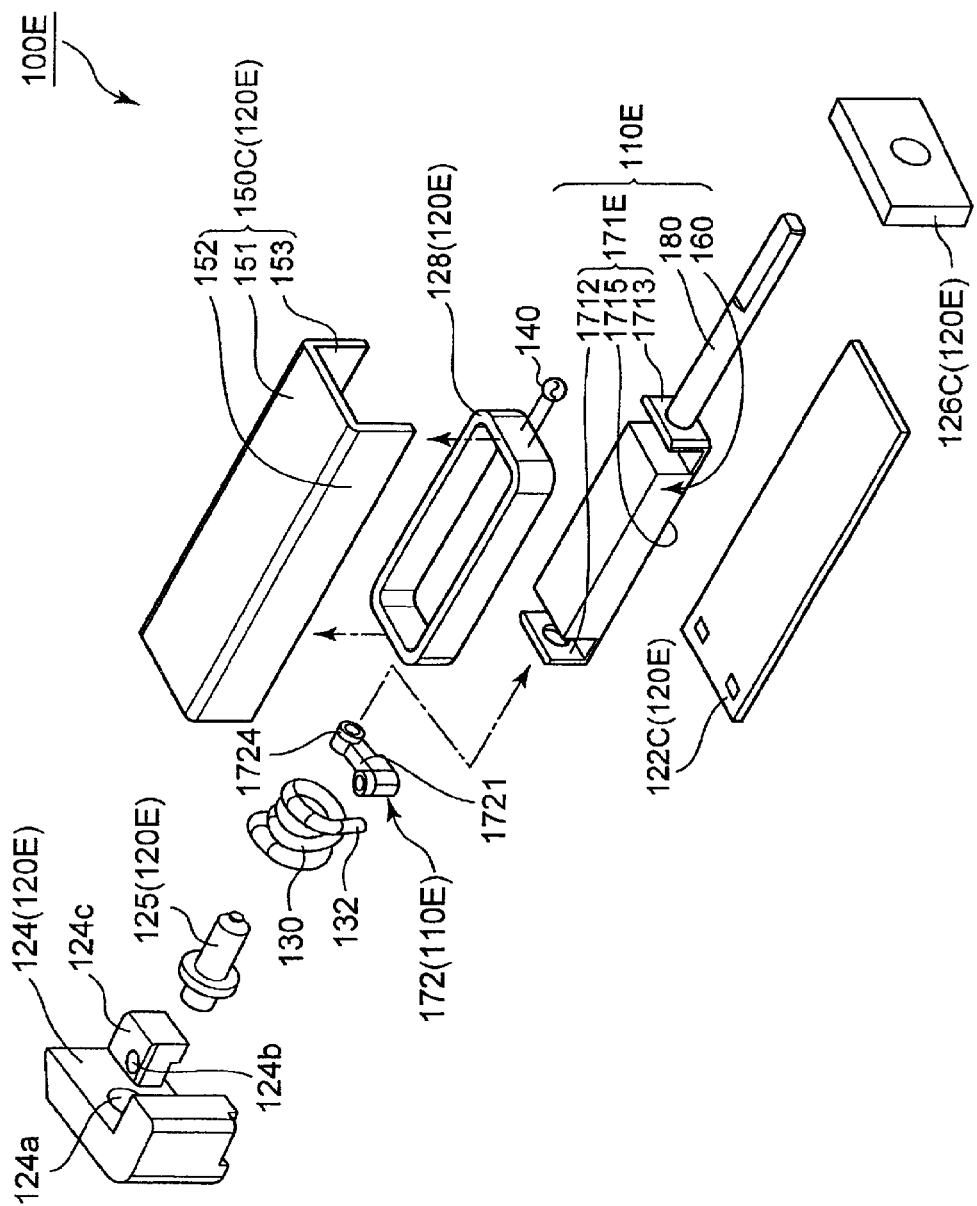
FIG. 21 is a principal-part exploded perspective view of an actuator according to a sixth embodiment of the present invention.
Figure 22:
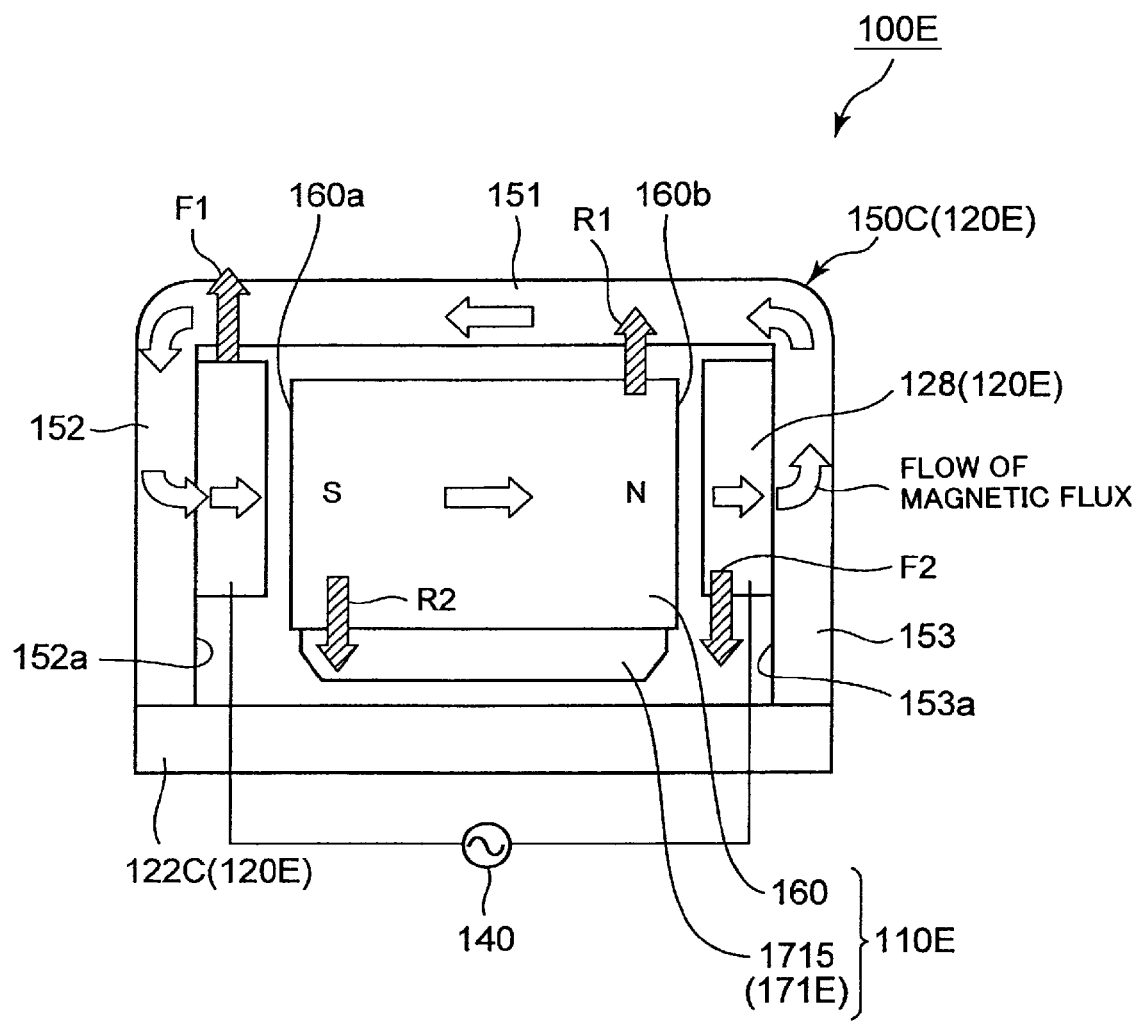
FIG. 22 is schematic cross-sectional view showing a movable body and fixed body of this actuator.

FIG. 21 is a principal-part exploded perspective view of actuator 100E according to a sixth embodiment of the present invention, and FIG. 22 is schematic cross-sectional view showing movable body 110E and fixed body 120E of this actuator 100E. FIG. 22 shows the flow of magnetic fluxes, from magnet 160 as a magnetic circuit of actuator 100E, with outline arrows.

Actuator 100E according to a sixth embodiment has the same magnetic circuit as in actuators 100 and 100A.

Assuming that the inertia of movable body 110E is J and the spring constant in a twisting direction is $k_{sp}$, actuator 100E satisfies equations 2 and 3 and is driven by the resonance frequency calculated by equation 1 above, with respect to fixed body 120E. This actuator 100E basically has the same configuration as actuator 100C according to the fourth embodiment, shown in FIG. 15 and FIG. 160, and therefore parts in actuator 100E that are the same as in actuator 100C will be assigned the same reference numerals and codes as in actuator 100C and their explanations will be omitted. This actuator 100E has basically the same magnetic circuit as in actuator 100C, except that magnet 160 is provided as a magnetic body, unlike actuator 100C in which coil 128 is the movable body.

Actuator 100E shown in FIG. 21 and FIG. 22 has fixed body 120E, movable body 110E, a twisted coil spring (hereinafter referred to as "coil spring"), which is elastic member 130 to support movable body 110E on fixed body 120E in a movable fashion, and alternating current supplying part 140.

As shown in FIG. 21, with this actuator 100E, when movable body 110E that is supported in fixed body 120E via elastic member 130 moves, output shaft 180 of movable body 110E rotates in forward and backward directions in a predetermined angle range, and outputs back-and-forth rotating vibration outside.

Fixed body 120E has base plate 122C, support wall parts 124 and 126C, outer yoke 150C, and coil 128 that is attached to outer yoke 150C. Meanwhile, movable body 110E has magnet (permanent magnet) 160, magnet holder 171E that is supported by support wall part 124 via a coil spring as elastic member 130 and that holds magnet 160, and output shaft 180.

In fixed body 120E, in outer yoke 150C, magnet 160 of movable body 110E is placed in an air gap on the inner side of coil 128. In actuator 100, by receiving as input an alternating current supply (AC voltage) from alternating current supplying part 140 in coil 128, movable body 110E is driven in a resonant state. The cycle of alternating current to be supplied is the same between embodiments (see FIG. 7) and overlapping explanations will be omitted.

Above the surface of base plate 122C, magnet 160 of movable body 110E is placed, and, surrounding this magnet 160, coil 128 is attached, via its outer periphery part, to opposing inner wall planes 152a and 153a of outer yoke 150C having a U-shaped cross section (including the shape of a letter U placed sideways).

Furthermore, support wall parts 124 and 126C are erected from edge parts of base plate 122C that are spaced apart in the long direction. The structure for supporting movable body 110E on fixed body 120E using support wall parts 124 and 126C, guide shaft 125, elastic member 130, joint part 172 and output shaft 180 is the same as with actuator 100C, and so descriptions will be omitted.

That is to say, in the coil spring being elastic member 130, one end part 131 is inserted in insertion hole 124b formed in fixed block 124c of support wall part 124, and opposite end part 132 is inserted in fitting hole 1721 formed in joint part 172. By this means, in the area surrounded by base plate 122C and outer yoke 150C, support wall part 124 is supported via elastic member 130, such that movable body 110E is able to move in twisting directions, about the axis of output shaft 180.

Outer yoke 150C is attached to base plate 122C in the same way as in the configuration of actuator 100C, and, with support wall parts 124 and 126C, forms a box shape to accommodate movable body 110E. Inside this box—to be more specific, in opposing inner wall planes 152a and 153a of side wall parts 152 and 153 of outer yoke 150—coil 128 that is wound to surround the periphery of magnet 160 of movable body 110E via an air gap is fixed.

Coil 128 is a voice coil here, and is placed such that its outer diameter parts are fixed on inner wall planes 152a and 153a of side wall parts 152 and 153 of outer yoke 150, and magnet 160 is placed on the inner side from the inner diameter parts, via air gaps from the inner periphery parts. That is to say, the inner periphery parts of coil 128 are placed to oppose the outer periphery planes of different poles of magnet 160 at a certain distance.

Also, between side wall parts 152 and 153 of outer yoke 150C, coil 128 has a square cylindrical shape formed by winding a coil wire around an axis to extend in a direction virtually perpendicular to yoke center part 151 of outer yoke 150, base plate 122C and output shaft 180. An alternating current of substantially the same frequency as a resonance frequency $f_0$ of movable body 110E is supplied from alternating current supplying part 140 to coil 128.

This coil 128 is attached on inner wall planes of outer yoke sidewall parts 152 and 153 closer to yoke center part 151 and is placed in locations to face different magnetic poles of magnet 160 (magnetic pole planes 160a and 160b).

Magnet (permanent magnet) 160, which is placed on the inner side of coil 128 via air gaps, is a cuboid having magnetic pole planes 160a and 160b that are long in the direction in which outer yoke 150C extends. Here, magnet 160 is held in a rotatable fashion in an air gap on the inner side of coil 170, by means of magnet holder 171E held rotatably by support wall parts 124 and 126C via elastic member 130.

This magnet holder 171E is formed in the shape of a letter U that is placed sideways on a side view, and that is open upward, as shown in FIG. 21. Magnet holder 171E has bottom plate part 1715 having a flat rectangular shape and front wall part 1713 and rear wall part 1712 that are erected from end parts that are spaced apart in the long direction of bottom plate part 1715 (that is, along the direction of extension of output shaft 180).

This magnet holder 171E is formed of a non-magnetic body. In front wall part 1713 of magnet holder 171E, output shaft 180 is attached perpendicularly. Furthermore, in rear wall part 1712 of magnet holder 171E, joint part 172 is attached such that the axial center of the coil spring of elastic member 130 that is connected to joint part 172 is placed to be virtually coaxial with output shaft 180. That is to say, output shaft 180 is attached to movable body 110E, approximately along the center of magnet 160, approximately parallel to varying magnetic pole planes 160a and 160b of magnet 160 (see FIG. 22), and to be located on an axis to pass the center of gravity movable body 110E.

Magnet holder 171E places magnet 160 apart from coil 128 and the back of yoke center part 151 of outer yoke 150C, and holds magnet 160 to be able to rotate in twisting direction about the axis of output shafts 180 and 126. In movable body 110E, coil 170 is placed between front wall part 1713 of magnet holder 171E and magnet 160 and between rear wall part 1712c and magnet 160, without making coil 128 touch these wall parts or magnet 160, so that movable body 110E is able to move on the inner side and outer side of coil 128.

Magnetic pole planes 160a and 160b of magnet 160, held by magnet holder 171E, are placed to oppose, entirely, the inner wall planes of outer yoke sidewall parts 152 and 153 via coil 128.

Here, the S-pole end (S magnetic pole plane 160a) of magnet 160 faces the inner wall plane 152a of sidewall part 152 of outer yoke 150C, and the N-pole side (N magnetic pole plane 160b) faces the inner wall plane 153a of sidewall part 153 of outer yoke 150C.

As shown in FIG. 21, output shaft 180 is provided to project outward from support wall part 126C in the same direction as the direction in which outer yoke 150C extends. By this means, in actuator 100, output shaft 180 is provided to project in a direction that is virtually perpendicular to the direction in which magnet 160 and sidewall parts 152 and 153 oppose each other over coil 128, from the center of sidewall parts 152 and 153.

When actuator 100 is used for an electric toothbrush, a toothbrush part is coaxially coupled with output shaft 180, and, at the head of this toothbrush part, a hair bundle part is provided to be perpendicular to the axial direction. By this means the toothbrush part moves in the same motion as output shaft 180, that is, moves in rolling motion, which is back-and-forth rotating vibration.

As shown in FIG. 22, with fixed body 120E and movable body 110E, outer yoke 150C, magnet 160 and coil 128 form a magnetic circuit.

To be more specific, actuator 100E has a magnetic circuit where magnetic fluxes produced from magnet 160 (designated by outline arrows) pass an air gap where coil 128 is placed, sidewall part 153 of outer yoke 150C, yoke center part 151, sidewall part 152 and the opposite air gap, in order, and continue to the opposite pole of magnet 160.

Similar to movable body 110C of actuator 100C, movable body 110E of this actuator 100E is supported by a spring mass system structure supported by fixed body 120E via elastic member 130. When an alternating current of the same frequency as resonance frequency $f_0$ of movable body 110E is supplied to coil 128 from alternating current supplying part 140, movable body 110E is driven in a resonant state efficiently. The back-and-forth rotating vibration that is produced then is transmitted from output shaft 180 to the outside.

Actuator 100E is driven based on the equation of motion represented by equation 2 above and based on the circuit equation represented by equation 3 above. That is to say, similar to actuator 100, the inertia moment, rotation angle, torque constant, current, spring constant, attenuation coefficient, and load torque in actuator 100C can be changed as adequate in a range to satisfy equation 2, and the voltage, resistance, inductance, and counter electromotive force multiplier can be changed as adequate in a range to satisfy equation 3.

The operation principle of movable body 110E of this actuator 100E is the same as actuator 100C and therefore will not be described in detail. FIG. 22 shows thrusts F1 and F2 of coil 128 when a forward current is applied, and thrusts R1 and R2 of magnet 160, which are reaction forces to these. When thrusts R1 and R2 are produced, movable body 110E moves in the directions of thrusts R1 and R2. When the direction of current changes, reverse thrusts to F1 and F2 work on coil 128, and, by this means, opposite thrusts to R1 and R2 work on magnet 160, and, consequently, movable body 110E moves in directions designated by reverse thrusts to R1 and R2. By repeating these, similar to the first embodiment, actuator 100E moves mobile body 120E in back-and-forth rotating vibration.

In actuator 100E, movable body 110E produces back-and-forth rotating motion (that is, back-and-forth rotating vibration), and this back-and-forth rotating vibration is sent outside via output shaft 180. When a toothbrush part is coupled with output shaft 180 and a hair bundle part is provided to be perpendicular to the axial direction at the head of this toothbrush part, the toothbrush part moves in back-and-forth rotating vibration and makes possible rolling brushing.

By this means, actuator 100E satisfies equations 2 and 3 and is driven by a resonance phenomenon using the resonance frequency represented by equation 1.

Furthermore, movable body 110E is formed with magnet 160 and magnet holder 171E, without using large-sized components like outer yoke 150C. Consequently, the scale of the inertia moment of movable body 110E does not depend on the outer shape and can be determined based upon the shape of magnet 160. Furthermore, given that magnet 160 is placed such that its center of gravity is located near output shaft 180 in movable body 110E, and, to be more specific, approximately on the axis of output shaft 180, so that magnet 160 is unlikely to be a factor to increase the inertia of movable body 110E. The increase of inertia moment due to change of the outer shape of actuator 100 is reduced, so that constraints are removed in terms of design, and it is therefore possible to improve the freedom of design with respct to actuator 100 itself. An electric toothbrush having actuator 100 provides the same advantage, so that it is possible to miniaturize the electric toothbrush itself.

Also, although with the configuration of actuator 100E according to the sixth embodiment base plate 122C is a non-magnetic body, this is by no means limiting, and it is equally possible to use a magnetic body. If base plate 122C in the configuration of actuator 100E is formed by a magnetic body, actuator 100E forms two paths for magnetic fluxes by magnet 160. That is to say, if base plate 122C in the configuration of actuator 100E is formed by a magnetic body, magnetic fluxes that are produced from magnet 160 reach sidewall part 153 of outer yoke 150C, from magnetic pole plane 160*b*, passing an air gap where coil 128 is placed. Next, from sidewall part 153, the magnetic fluxes pass both yoke center part 151 and base plate 112G on the opposite side from yoke center part 151, and then arrive at sidewall part 153. Magnetic fluxes pass sidewall part 152 and the opposite air gap in order, and continue to the opposite pole of magnet 160 (magnetic pole plane 160*a*). By this means, the magnetic saturation in the magnetic circuit is reduced, so that it is possible to increase the thrust of movable body 110E that is produced when an AC voltage is supplied from alternating current supplying part 140 to coil 128. That is to say, in actuator 100E, it is possible to prevent magnetic fluxes from leaking from the magnetic circuit including base plate 122C, outer yoke 150C, magnet 160 and coil 128.

Furthermore, outer yoke 150 according to the above embodiments can be configured in any way as long as there are inner wall planes to oppose different magnetic poles of magnet 160, and a magnetic circuit is formed with coil 128 and magnet 160, and it is possible to, for example, form the entirety of outer yoke 150 to have an arc-shaped cross section or make the main body of the yoke a arc shape.

Various changes can be made to the present invention without departing from the spirit of the present invention, and such changes are certainly within the scope of the present invention.

The disclosure of Japanese Patent Application No. 2008-292631, filed on Nov. 14, 2008, including the specification, drawings, and abstract, is incorporated herein by reference in its entirety.

INDUSTRIAL APPLICABILITY

An actuator according to the present invention provides an advantage of realizing back-and-forth rotating motion of an electric toothbrush or the like without using a drive transmitting mechanism apart from a drive source and allowing miniaturization of an electric toothbrush or the like, and therefore is suitable for use as an actuator that is used for an electric toothbrush or the like to produce back-and-forth rotating vibration.

REFERENCE SIGNS LIST

100, 100A, 100B, 100C, 100D, 100E Actuator
110, 110B, 110C, 110D, 110E Movable body
120, 120B, 120C, 120D, 120E Fixed body
122, 122C, 122D Base plate
127 Bearing
128 Coil
130 Elastic member
131 One end part
132 Opposite end part
140 Alternating current supplying part
150, 150C Outer yoke
151 Yoke center part
152, 153 Sidewall part
152*a*, 153*a* Inner wall part
160 Magnet
160*a*, 160*b* Magnetic pole plane
170, 170C Non-magnetic body
170B, 170D Projection part
171 Yoke holder
171C, 171D Coil holder
171E Magnet holder
172 Joint part
180 Output shaft
190 Wire-shaped spring body
191 Base plate fixing part
192 Yoke fixing part
193 Arm part

The invention claimed is:

1. An actuator comprising:
    an outer yoke having inner wall planes opposing each other, the inner wall planes being placed a predetermined interval apart;
    a permanent magnet that has different magnetic pole planes facing the inner wall planes respectively over air gaps therebetween;
    a coil that is placed through the air gaps and surrounds the permanent magnet;
    a fixed body that has one of the permanent magnet or the coil;
    a movable body that has the other one of the permanent magnet or the coil and that has an output shaft that is perpendicular to both a direction in which the magnetic pole planes and the inner wall planes face each other and an axial direction of winding of the coil;
    an alternating current supplying section that supplies an alternating current to the coil, the alternating current having a frequency substantially the same as a resonance frequency of the movable body; and
    one coil spring that is placed between a rear wall part of the fixed body and a rear wall part of the movable body and that has an end fixed to the fixed body and another end fixed to the movable body, and that supports the movable body on the fixed body in such a way that the movable body is able to rotate about an axis along the output shaft,
    wherein the coil spring connects the fixed body and the movable body in such a way that an axial center of a winding part in the coil spring is substantially matches an axial center of the output shaft, and
    wherein the movable body is supported via the coil spring in such a way that the movable body is able to move in a twisting direction of the output shaft.

2. The actuator according to claim 1, wherein:
    the movable body comprises the outer yoke and the permanent magnet that is provided in the outer yoke via a non-magnetic body; and
    the fixed body comprises the coil.

3. The actuator according to claim 1, wherein:
    the movable body comprises the coil; and
    the fixed body comprises the outer yoke and the permanent magnet that is provided in the outer yoke via a non-magnetic body.

4. The actuator according to claim 1, wherein the movable body is axially supported on the fixed body in such a way that the movable body is able to rotate about the output shaft.

5. An electric toothbrush comprising:
the actuator of claim 1; and
a toothbrush part that is coaxially coupled with the output shaft of the actuator, a head of the toothbrush part being provided with bristles perpendicular to an axial direction of the output shaft.

* * * * *